United States Patent
Ried et al.

(10) Patent No.: US 9,075,062 B2
(45) Date of Patent: Jul. 7, 2015

(54) IDENTIFICATION OF BIOMARKERS BY SERUM PROTEIN PROFILING

(75) Inventors: Thomas Ried, Bethesda, MD (US); Jens Habermann, Celle (DE)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 1876 days.

(21) Appl. No.: 11/886,886

(22) PCT Filed: Mar. 22, 2006

(86) PCT No.: PCT/US2006/010624
§ 371 (c)(1),
(2), (4) Date: Dec. 11, 2008

(87) PCT Pub. No.: WO2006/102526
PCT Pub. Date: Sep. 28, 2006

(65) Prior Publication Data
US 2009/0142332 A1    Jun. 4, 2009

Related U.S. Application Data

(60) Provisional application No. 60/664,681, filed on Mar. 22, 2005.

(51) Int. Cl.
C12Q 1/00 (2006.01)
G01N 33/53 (2006.01)
G01N 33/574 (2006.01)

(52) U.S. Cl.
CPC ............................. G01N 33/57419 (2013.01)

(58) Field of Classification Search
CPC .............................................. G01N 33/57419
See application file for complete search history.

(56) References Cited

U.S. PATENT DOCUMENTS

2003/0054366 A1    3/2003    Schlegel et al.
2004/0053304 A1    3/2004    Markowitz
2005/0048534 A1    3/2005    Macina et al.

FOREIGN PATENT DOCUMENTS

WO    WO 2004/090550 A2 * 10/2004 ............. G01N 33/68

OTHER PUBLICATIONS

Juhl et al. (J. Surg. Oncol. 1997 64:222-230).*
Faradji et al. (Internatl. J. Artificial Organs, 1991, 14:109-115).*
Roboz et al (Proc Amer. Assoc. Cancer Res. vol. 45, Mar. 1, 2004, abstract # 3551).*
Tresca. A. (About.com Mar. 12, 2005).*
Rudin et al. (Clinical Cancer Res. May 2001, 7:1214-1220).*
Kufe et al. (Cancer Medicine 6, BC Decker, 2003).*
National Cancer Institute Dictionary of Cancer Terms (adenoma http://www.cancer.gov/dictionary/?print=1&cdrid=46217, Apr. 8, 2014).*
Yu et al., "An integrated approach to the detection of colorectal cancer utilizing proteomics and bioinformatics", *World J. Gastroenterol*, 10(21), pp. 3127-3131 (2004).
David B. Friedman, et al. "Proteome Analysis of Human Colon Cancer By Two-Dimensional Difference Electrophoresis and Mass Spectrometry" Proteomics 4:793-811, Feb. 2004.
Sudhir Srivastava et al. "Biomarkers for Early Detection of Colon Cancer," Clinical Cancer Research 7:1118-26, May 2001.
L.M. Hunt et al, "Chemical and Immunological Testing for Faecal Occult Blood in Screening Subjects at Risk of Familial Colorectal Cancer" Gut 40:110-112, 1997.

* cited by examiner

*Primary Examiner* — Peter J Reddig
(74) *Attorney, Agent, or Firm* — Locke Lord LLP

(57) ABSTRACT

The present invention relates to methods of determining colorectal cancer status in a subject. The invention further relates to kits for determining colorectal cancer status in a subject. The invention further related to methods of identifying biomarker for determining colorectal cancer status in a subject.

14 Claims, 7 Drawing Sheets

IDENTIFICATION OF BIOMARKERS BY SERUM PROTEIN PROFILING

RELATED APPLICATIONS

This application is a National Stage Application of International Application PCT/US2006/10624 having an International filing date of Mar. 22, 2006, which claims the benefit of U.S. Provisional application No. 60/664,681, filed Mar. 22, 2005. Each of these applications are incorporated herein by reference in their entirety.

GOVERNMENT SUPPORT

This work described herein was supported by the National Institutes of Health.

BACKGROUND OF THE INVENTION

Detection of cancer at early stages is critical for curative treatment interventions. While the five-year disease free survival for UICC stage I tumors exceeds 90%, this percentage is reduced to 63% in UICC stage III carcinomas (O'Connell J B, Maggard M A, Ko C Y. Colon cancer survival rates with the new American Joint Committee on Cancer sixth edition staging. J Natl Cancer Inst 2004; 96: 1420-1425). Tools and methodologies for early cancer detection directly impact survival times.

Late diagnosis of colorectal carcinomas results in a significant reduction of average survival times. Yet, despite screening programs about 70% of tumors are detected at advanced stages (UICC III/IV).

In present clinical practice, for example, screening for cancer and pre-invasive polyps of the colorectum is based on clinical examination, the detection of fecal occult blood (FOBT), and on sigmoidoscopy or colonoscopy (Mak T, Lalloo F, Evans D G, Hill J. Molecular stool screening for colorectal cancer. Br J Surg 2004; 91:790-800). The successful implementation of these screening procedures has contributed to a modest reduction of the mortality of colorectal carcinomas (Fleischer D E, Goldberg S B, Browning T H, Cooper J N, Friedman E, Goldner F H, Keeffe E B, Smith L E. Detection and surveillance of colorectal cancer. Jama 1989; 261:580-585). However, colonic tumors still rank among the most common malignant cancers in the Western World and present a major health care problem. Approximately 140,000 new cases are diagnosed in the U.S. annually, and about 55,000 subjects die of the disease (Schulmann K, Reiser M, Schmiegel W. Colonic cancer and polyps. Best Pract Res Clin Gastroenterol 2002; 16:91-114). The high mortality is attributable to a low compliance to some screening tests (e.g., colonoscopy) or to the low sensitivity of others (e.g., FOBT) (Schulmann, et al.).

Current methods for early detection, diagnosis, prognosis, and treatment of cancer fails to satisfactorily reduce the morbidity associated with the disease. There is thus a need in the art for further reduction of mortality rates, and early cancer detection in minimally invasive, cost efficient formats.

SUMMARY

The present invention provides, for the first time, novel protein markers that are differentially present in the samples of colon cancer subjects and in the samples of control subjects. The present invention also provides sensitive and quick methods and kits that are useful for determining the colorectal cancer status by measuring these novel markers. The measurement of these markers alone or in combination, in patient samples provides information that a diagnostician can correlate with a probable diagnosis of human cancer or a negative diagnosis (e.g., normal or disease-free). The markers are characterized by their m/z value or molecular weight, respectively and/or by their known protein identities. The markers can be resolved from other proteins in a sample by using a variety of fractionation techniques, e.g., chromatographic separation coupled with mass spectrometry, protein capture using immobilized antibodies or by traditional immunoassays.

In preferred embodiments, the method of resolution involves Surface-Enhanced Laser Desorption/Ionization ("SELDI") mass spectrometry, in which the surface of the mass spectrometry probe comprises adsorbents that bind the markers.

The present invention provides a method of qualifying colorectal cancer status in a subject comprising measuring at least one biomarker in a sample from the subject.

In one aspect, the invention provides biomarkers for colorectal cancer status comprising one or more of the following Markers, which are centered around the values, given in Daltons: Marker I: 2172.8 Da, Marker II: 2591.1 Da, Marker III: 2646.9 Da, Marker IV: 5715.9 Da, Marker V: 7005.2 Da, Marker VI: 7568.9 Da, Marker VII: 7683.6 Da, Marker VIII: 7722.6 Da, Marker IX: 7905.8 Da, Marker X: 9148.7 Da, Marker XI: 9556.6 Da, Marker XII: 14653.8 Da, Marker XIII: 14698.6 Da, and combinations thereof. These Markers I-XIV are set forth in Table I, which follows and are sometimes referred to herein as biomarkers of Table I or similar designations.

In one embodiment, the biomarker for colorectal cancer status of the invention comprises Marker X: 9148.7.

In certain embodiments, the biomarkers may be used in combination, for example, Marker IV: 5715.9 Da and Marker X: 9148.7 Da; Marker X: 9148.7 Da and Marker XI: 9556.6 Da; Marker II: 2591.1 Da, Marker X: 9148.7 Da, and Marker XII: 14653.8 Da; Marker VI: 7568.9 Da, Marker X: 9148.7 Da, and Marker XII: 14653.8 Da; Marker VII: 7683.6 Da, Marker X: 9148.7 Da, and Marker XII: 14653.8 Da; Marker IX: 7905.8 Da, Marker X: 9148.7 Da, Marker I: 2172.8 Da, and Marker III: 2646.9 Da; Marker V: 7005.2 Da, Marker VIII: 7722.6 Da, Marker X: 9148.7 Da, Marker XIII: 14698 Da, and Marker III: 2646.9 Da; Marker V: 7005.2 Da, Marker IX: 7905.8 Da, Marker X: 9148.7 Da, Marker XII: 14653.8 Da, and Marker III: 2646.9 Da; or Marker I: 2172.8 Da, Marker II: 2591.1 Da, Marker III: 2646.9 Da, Marker IV: 5715.9 Da, Marker V: 7005.2 Da, Marker VI: 7568.9 Da, Marker VII: 7683.6 Da, Marker VIII: 7722.6 Da, Marker IX: 7905.8 Da, Marker X: 9148.7 Da, Marker XI: 9556.6 Da, Marker XII: 14653.8 Da, and Marker XIII: 14698.6 Da.

The invention provides, in one aspect, methods for qualifying colorectal cancer status in a subject comprising measuring at least one biomarker in a sample from the subject, wherein the biomarker is selected from one or more of the biomarkers of Table 1, and correlating the measurement with colorectal cancer status.

In one embodiment, the colorectal cancer is adenocarcinoma, mucinous adenocarcinoma, signet-ring cell adenocarcinoma, squamous cell carcinoma, adenosquamous carcinoma, undifferentiated carcinoma, unclassified carcinoma, carcinoid tumors, or nonepithelial tumors.

In one embodiment, the method further comprises managing subject treatment based on the status.

In a related embodiment the managing subject treatment is selected from ordering further diagnostic tests (e.g., colonoscopy and imaging techniques), administering at least one therapeutic agent, administering radiation therapy, immunotherapy, hyperthermia, surgery, surgery followed or preceded by chemotherapy and/or radiation therapy, biotherapy, and taking no further action.

In another related embodiment, the therapeutic agent is selected from one or more of hypomethylating agents, farnesyltransferase inhibitors, cytokines, immunomodulatory agents, hormones, and antibodies. The therapeutic agents may be selected from one or more of folic acid, fluorouracil, 5-FU irinotecan, oxaliplatin, leucovorin, 5-FU, irinotecan, levamisole, and low-dose leucovorin. Combination therapies of the invention also include, for example, AIO regimen (folic acid, fluorouracil (5-FU irinotecan), FOLFOX4 regimen (oxaliplatin, leucovorin, 5-FU), FOLFOX6 regimen (oxaliplatin, leucovorin, 5-FU), FOLFIRI regimen (folic acid, 5-FU, irinotecan), IFL (or Saltz) regimen (irinotecan, 5-FU, leucovorin), NCCTG regimen (5-FU, levamisole), or NCCTG regimen (5-FU, low-dose leucovorin).

In one embodiment, the method for qualifying colorectal cancer status in a subject may further comprise measuring the at least one biomarker after subject management.

In another embodiment, the colorectal cancer status is selected from one or more of the subject's risk of colorectal carcinoma, the presence or absence of carcinoma, the type of carcinoma disease, the stage of carcinoma and effectiveness of treatment.

The invention provides, in another aspect, methods for differentiating between a diagnosis of colorectal cancer and non-colorectal cancer comprising detecting in a subject sample an amount of at least one biomarker wherein the biomarker is selected from one or more of the biomarkers of Table 1, and correlating the amount with a diagnosis of colorectal cancer or non-colorectal cancer.

TABLE 1

| MARKER | Da or Name |
| --- | --- |
| Marker I | 2172.8 |
| Marker II | 2591.1 |
| Marker III | 2646.9 |
| Marker IV | 5715.9 |
| Marker V | 7005.2 |
| Marker VI | 7568.9 |
| Marker VII | 7683.6 |
| Marker VIII | 7722.6 |
| Marker IX | 7905.8 |
| Marker X | 9148.7 |
| Marker XI | 9556.6 |
| Marker XII | 14653.8 |
| Marker XIII | 14698.6 |
| Marker XIV | C3a anaphylatoxin |

Markers of the invention may be detected, for example, by mass spectrometry according to one embodiment. In a related embodiment, the markers are detected by SELDI. In another related embodiment, the marker or markers are detected by capturing the marker on a biochip having a hydrophobic surface and detecting the captured marker by SELDI. Suitable biochips include the IMAC3 ProteinChip® Array and the WCX2 ProteinChip® Array.

In one embodiment, the methods for qualifying colorectal cancer status in a subject further comprise generating data on immobilized subject samples on a biochip, by subjecting the biochip to laser ionization and detecting intensity of signal for mass/charge ratio; and transforming the data into computer readable form; executing an algorithm that classifies the data according to user input parameters, for detecting signals that represent biomarkers present in colorectal cancer subjects and are lacking in non-colorectal cancer subject controls.

In one embodiment, one or more of the biomarkers are detected using laser desorption/ionization mass spectrometry, comprising providing a probe adapted for use with a mass spectrometer comprising an adsorbent attached thereto; contacting the subject sample with the adsorbent; desorbing and ionizing the biomarker or biomarkers from the probe; and detecting the desorbed/ionized markers with the mass spectrometer.

In one embodiment, least one or more protein biomarkers are detected using immunoassays.

In one embodiment, the methods for qualifying colorectal cancer status in a subject further comprise measuring the amount of each biomarker in the subject sample and determining the ratio of the amounts between the markers. In a related embodiment, the measuring is selected from detecting the presence or absence of the biomarkers(s), quantifying the amount of marker(s), and qualifying the type of biomarker.

In one embodiment, the protein biomarkers are measured by one or more of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS).sub.n, quadrupole mass spectrometry, fourier transform mass spectrometry (FTMS), and ion trap mass spectrometry, where n is an integer greater than zero.

In one embodiment, the correlating is performed by a software classification algorithm.

The invention provides kits, for example, for aiding the diagnosis of colorectal cancer or the diagnosis of the subtypes of colorectal cancer. The kits may suitably include an adsorbent, wherein the adsorbent retains one or more biomarkers selected from one or more of the markers of Table 1, and written instructions for use of the kit for detection of colorectal cancer.

In one aspect, the invention provides methods for identifying a candidate compound for treating colorectal cancer comprising contacting one or more of the biomarkers of Table 1 with a test compound; and determining whether the test compound interacts with the biomarker, wherein a compound that interacts with the biomarker is identified as a candidate compound for treating colorectal cancer.

The invention also provides methods of treating colorectal cancer comprising administering to a subject suffering from or at risk of developing colorectal cancer a therapeutically effective amount of a compound capable of modulating the expression or activity of one or more of the biomarkers of Table 1. In another aspect, the invention provides methods of treating a condition in a subject comprising administering to a subject a therapeutically effective amount of a compound which modulates the expression or activity of one or more of the biomarkers of Table 1.

In certain embodiments, the compound are selected from the group consisting of enzyme inhibitors, cytotoxic drugs, cytokins, chemokines, antibodies, a DNA molecule, an RNA molecule, a small molecule, a peptide, and a peptidomimetic.

Provided herein are software products comprising code that accesses data attributed to a sample, the data comprising measurement of at least one biomarker in the sample, the biomarker selected from the group consisting of the biomarkers of Table 1; and code that executes a classification algorithm that classifies the colorectal cancer status of the sample as a function of the measurement.

In one embodiment, the classification algorithm classifies the colorectal cancer status of the sample further as a function of the measurement of any one or more of Marker I-XIV.

According to one aspect, the invention provides methods for modulating the concentration of a biomarker, wherein the biomarker is one or more of the biomarkers listed in Table 1. The method comprises contacting a cell with a test compound, measuring at least one biomarker, wherein the biomarker is selected from one or more of the biomarkers of Table 1, and correlating the measurement with a determination of efficacy.

The invention provides in one aspect, a software product for identifying biomarkers comprising an algorithm for determining distance dependant K nearest neighbors.

The invention also provides, in one aspect, a method of identifying a biomarker comprising obtaining two SELDI spectra from a sample; subtracting the background from the spectra; truncating the spectra; scaling the peaks of the spectra; reducing the peaks of the spectra; determining if the two spectra should be combined; optionally combining the at least two spectra; and determining the distance dependent K-nearest neighbors.

In one embodiment, the truncating is eliminating mass to charge ratios (m/z) values below 1500 Da. In a related embodiment, the scaling comprises totaling the ion current to from between about 20000 to about 70000 for the sample. In another related embodiment, the combining is averaging the at least two spectra or keeping the spectra as duplicates. In yet another related embodiment, significant peaks are greater than 15% of the average intensity of a bin in the combined spectrum and not within 0.3% (M/Z) of a previously selected peak.

The methods of identifying a biomarker may further comprise identifying significant peaks from the combined spectra. The methods may also further comprise searching for outlier spectra.

In one aspect, the invention provides, a method of identifying a biomarker comprising determining distant dependent K-nearest neighbors.

The invention also provides methods of determining the colorectal cancer status of a subject, comprising (a) obtaining a biomarker profile from a sample taken from the subject; and (b) comparing the subject's biomarker profile to a reference biomarker profile obtained from a reference population, wherein the comparison is capable of classifying the subject as belonging to or not belonging to the reference population; wherein the subject's biomarker profile and the reference biomarker profile comprise one or more markers listed in Table 1.

In one embodiment, the comparison of the biomarker profiles can determine colorectal cancer status in the subject with an accuracy of at least about 60%, 70%, 80%, 90% or approaching 100%.

In certain embodiments, the sample is fractionated by one or more of chemical extraction partitioning, ion exchange chromatography, reverse phase liquid chromatography, isoelectric focusing, one-dimensional polyacrylamide gel electrophoresis (PAGE), two-dimensional polyacrylamide gel electrophoresis (2D-PAGE), thin-layer chromatography, gas chromatography, liquid chromatography, and any combination thereof.

The invention also provides, in one aspect, processes for the purification of a biomarker, comprising fractioning a sample comprising one or more protein biomarkers by size-exclusion chromatography and collecting a fraction that includes the one or more biomarkers; and/or fractionating a sample comprising the one or more biomarkers by anion exchange chromatography and collecting a fraction that includes the one or more biomarkers, wherein the biomarker is selected from one or more of the biomarkers of Table 1.

In other methods, the measuring step comprises quantifying the amount of marker(s) in the sample. In other methods, the measuring step comprises qualifying the type of biomarker in the sample.

While the absolute identity of all of these markers is not yet known, such knowledge is not necessary to measure them in a patient sample, because they are sufficiently characterized by, e.g., mass and by affinity characteristics. It is noted that molecular weight and binding properties are characteristic properties of these markers and not limitations on means of detection or isolation. Furthermore, using the methods described herein or other methods known in the art, the absolute identity of the markers can be determined.

The present invention also relates to biomarkers designated as Markers I through XIV. Protein markers of the invention can be characterized in one or more of several respects. In particular, in one aspect, these markers are characterized by molecular weights under the conditions specified herein, particularly as determined by mass spectral analysis. In another aspect, the markers can be characterized by features of the markers' mass spectral signature such as size (including area) and/or shape of the markers' spectral peaks, features including proximity, size and shape of neighboring peaks, etc. In yet another aspect, the markers can be characterized by affinity binding characteristics, particularly ability to binding to cation-exchange and/or hydrophobic surfaces. In preferred embodiments, markers of the invention may be characterized by each of such aspects, i.e. molecular weight, mass spectral signature and cation and/or hydrophobic absorbent binding.

For the mass values of the markers disclosed herein, the mass accuracy of the spectral instrument is considered to be about within +/−0.15 percent of the disclosed molecular weight value. Additionally, to such recognized accuracy variations of the instrument, the spectral mass determination can vary within resolution limits of from about 400 to 1000 m/dm, where m is mass and dm is the mass spectral peak width at 0.5 peak height. Those mass accuracy and resolution variances associated with the mass spectral instrument and operation thereof are reflected in the use of the term "about" in the disclosure of the mass of each of Markers I through XIV. It is also intended that such mass accuracy and resolution variances and thus meaning of the term "about" with respect to the mass of each of the markers disclosed herein is inclusive of variants of the markers as may exist due to sex, genotype and/or ethnicity of the subject and the particular cancer or origin or stage thereof.

Each of Markers I-XIV also is characterized by its ability to bind to a ProteinChip adsorbent (e.g., IMAC3 or WCX2), as specified herein.

In a preferred embodiment, the present invention provides for a method for detecting, and diagnosing (including e.g., differentiating between) different subtypes of colorectal cancer, wherein the method comprises using a biochip array for detecting at least one biomarker in a subject sample; evaluating at least one biomarker in a subject sample, and correlating the detection of one or more protein biomarkers with a colorectal cancer subtype.

The biomarkers of the invention may be detected in samples of blood, blood plasma, serum, urine, tissue, cells, organs, seminal fluids, bone marrow, and cerebrospinal fluid.

Preferred detection methods include use of a biochip array. Biochip arrays useful in the invention include protein and nucleic acid arrays. One or more markers are captured on the biochip array and subjected to laser ionization to detect the molecular weight of the markers. Analysis of the markers is, for example, by molecular weight of the one or more markers against a threshold intensity that is normalized against total ion current.

In preferred methods of the present invention, the step of correlating the measurement of the biomarkers with colorectal cancer status is performed by a software classification algorithm. Preferably, data is generated on immobilized subject samples on a biochip array, by subjecting the biochip array to laser ionization and detecting intensity of signal for mass/charge ratio; and transforming the data into computer readable form; and executing an algorithm that classifies the data according to user input parameters, for detecting signals that represent markers present in colorectal cancer subjects and are lacking in non-colorectal cancer subject controls.

Preferably the biochip surfaces are, for example, ionic, anionic, hydrophobic; comprised of immobilized nickel or copper ions; comprised of a mixture of positive and negative ions; and/or comprised of one or more antibodies, single or double stranded nucleic acids, proteins, peptides or fragments thereof, amino acid probes, or phage display libraries.

In other preferred methods one or more of the markers are measured using laser desorption/ionization mass spectrometry, comprising providing a probe adapted for use with a mass spectrometer comprising an adsorbent attached thereto, and contacting the subject sample with the adsorbent, and desorbing and ionizing the marker or markers from the probe and detecting the deionized/ionized markers with the mass spectrometer.

Preferably, the laser desorption/ionization mass spectrometry comprises: providing a substrate comprising an adsorbent attached thereto; contacting the subject sample with the adsorbent; placing the substrate on a probe adapted for use with a mass spectrometer comprising an adsorbent attached thereto; and desorbing and ionizing the marker or markers from the probe and detecting the desorbed/ionized marker or markers with the mass spectrometer.

The adsorbent can for example be, hydrophobic, hydrophilic, ionic or metal chelate adsorbent, such as nickel or copper ions; or an antibody, single- or double stranded oligonucleotide, amino acid, protein, peptide or fragments thereof.

In another embodiment, a process for purification of a biomarker, comprising fractioning a sample comprising one or more protein biomarkers by size-exclusion chromatography and collecting a fraction that includes the one or more biomarker; and/or fractionating a sample comprising the one or more biomarkers by anion exchange chromatography and collecting a fraction that includes the one or more biomarkers. Fractionation is monitored for purity on normal phase and immobilized nickel arrays. Generating data on immobilized marker fractions on an array is accomplished by subjecting the array to laser ionization and detecting intensity of signal for mass/charge ratio; and transforming the data into computer readable form; and executing an algorithm that classifies the data according to user input parameters, for detecting signals that represent markers present in colorectal cancer subjects and are lacking in non-colorectal cancer subject controls. Preferably fractions are subjected to gel electrophoresis and correlated with data generated by mass spectrometry. In one aspect, gel bands representative of potential markers are excised and subjected to enzymatic treatment and are applied to biochip arrays for peptide mapping.

In another aspect one or more biomarkers are selected from gel bands representing Markers I-XIV described herein.

Purified proteins for detection of colorectal cancer and/or screening and aiding in the diagnosis of colorectal cancer and/or generation of antibodies for further diagnostic assays are provided.

In further embodiments, the invention provides methods for identifying compounds (e.g., antibodies, nucleic acid molecules (e.g., DNA, RNA), small molecules, peptides, and/or peptidomimetics) capable of treating colorectal cancer comprising contacting at least one or more of a biomarker selected from Markers I-XIV, and combinations thereof with a test compound; and determining whether the test compound interacts with, binds to, or modulates the biomarker, wherein a compound that interacts with, binds to, or modulates the biomarker is identifies as a compound capable of treated colorectal cancer.

In another embodiment, the invention provides methods of treating colorectal cancer comprising administering to a subject suffering from or at risk of developing colorectal cancer a therapeutically effective amount of a compound (e.g., an antibody, nucleic acid molecule (e.g., DNA, RNA), small molecule, peptide, and/or peptidomimetic) capable of modulating the expression or activity of one or more of the biomarkers I-XIV.

Thus, the methods of the present invention provide and solve the need for methods of accurately assessing, i.e., diagnostically, prognostically, and therapeutically, cancer, including colorectal cancer.

In one aspect, presented here is a biomarker comprising C3a anaphylatoxin. This biomarker may be a marker of colorectal cancer status.

In one embodiment, the C3a anaphylatoxin comprises one or more mz values at about 9148.7 or 8941.1.

In another embodiment, the maximum intensities of the mz values are about 78.8 or 246.3.

In one embodiment, wherein sensitivity of colorectal cancer diagnosis is from between about 90 to about 99%.

In one embodiment, sensitivity of colorectal cancer diagnosis is from between about 95.8 to about 97.8%.

In another embodiment, specificity of colorectal cancer diagnosis is from between about 90 to about 99%.

In one embodiment, specificity of colorectal cancer diagnosis is from between about 95.2 to about 97.2%.

In one aspect, presented herein is a biomarker comprising C3a-desArg. his biomarker may be a marker of colorectal cancer status.

In one embodiment, the m/z value comprises 9148.

In another embodiment, C3a-desArg is the stable form of C3a anaphylatoxin. For example, the m/z 9148 detect the stable form of C3a anaphylatoxin, e.g., C3a-desArg.

Other embodiments of the invention are disclosed infra.

DEFINITIONS

Figure 1:
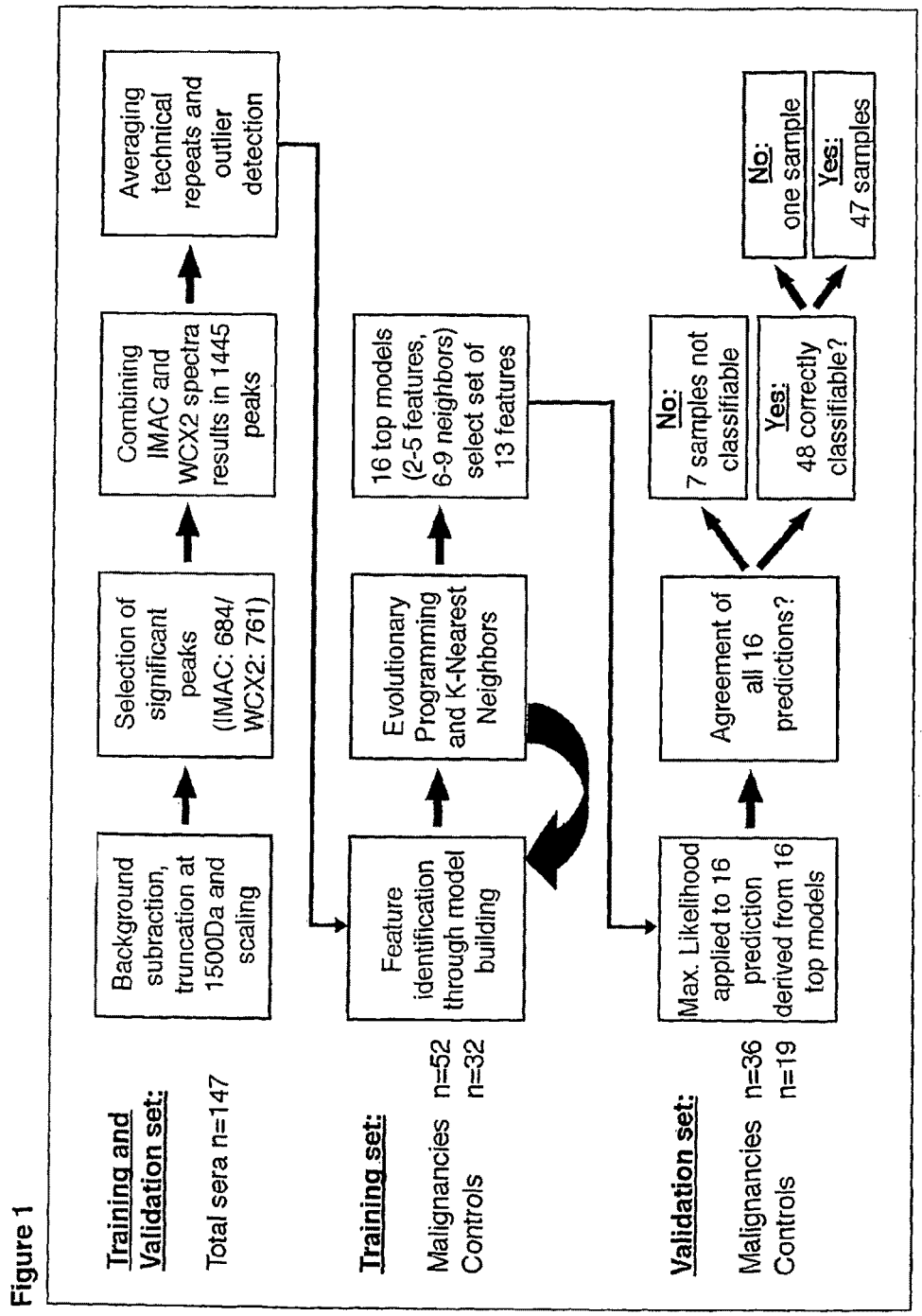
FIG. 1 depicts a flow-chart of analytical procedures for class prediction by SELDI-TOF based serum protein profiling.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

The term "colorectal cancer status" refers to the status of the disease in the patient. Examples of types of colorectal cancer statuses include, but are not limited to, the subject's risk of cancer, including colorectal carcinoma, the presence or absence of disease (e.g., carcinoma), the stage of disease in a patient (e.g., carcinoma), and the effectiveness of treatment of disease. Other statuses and degrees of each status are known in the art.

The term "unfractionated" or "whole serum" refers the biomarkers that are isolated from unfractionated serum and placed on a hydrophobic chip such as the IMAC3 (immobilized metal affinity capture array with a nitriloacetic acid (NTA) surface) or the WCX2 (weak cation exchange array with carboxylate functionality).

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

"Laser desorption mass spectrometer" refers to a mass spectrometer that uses laser energy as a means to desorb, volatilize, and ionize an analyte.

"Tandem mass spectrometer" refers to any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, Fourier transform ion cyclotron resonance mass spectrometers, electrostatic sector-magnetic sector mass spectrometers, and combinations thereof.

"Mass analyzer" refers to a sub-assembly of a mass spectrometer that comprises means for measuring a parameter that can be translated into mass-to-charge ratios of gas phase ions. In a time-of-flight mass spectrometer the mass analyzer comprises an ion optic assembly, a flight tube and an ion detector.

"Ion source" refers to a sub-assembly of a gas phase ion spectrometer that provides gas phase ions. In one embodiment, the ion source provides ions through a desorption/ ionization process. Such embodiments generally comprise a probe interface that positionally engages a probe in an interrogatable relationship to a source of ionizing energy (e.g., a laser desorption/ionization source) and in concurrent communication at atmospheric or subatmospheric pressure with a detector of a gas phase ion spectrometer.

Forms of ionizing energy for desorbing/ionizing an analyte from a solid phase include, for example: (1) laser energy; (2) fast atoms (used in fast atom bombardment); (3) high energy particles generated via beta decay of radionucleides (used in plasma desorption); and (4) primary ions generating secondary ions (used in secondary ion mass spectrometry). The preferred form of ionizing energy for solid phase analytes is a laser (used in laser desorption/ionization), in particular, nitrogen lasers, Nd-Yag lasers and other pulsed laser sources. "Fluence" refers to the energy delivered per unit area of interrogated image. A high fluence source, such as a laser, will deliver about 1 mJ/mm2 to 50 mJ/mm2. Typically, a sample is placed on the surface of a probe, the probe is engaged with the probe interface and the probe surface is struck with the ionizing energy. The energy desorbs analyte molecules from the surface into the gas phase and ionizes them.

Other forms of ionizing energy for analytes include, for example: (1) electrons that ionize gas phase neutrals; (2) strong electric field to induce ionization from gas phase, solid phase, or liquid phase neutrals; and (3) a source that applies a combination of ionization particles or electric fields with neutral chemicals to induce chemical ionization of solid phase, gas phase, and liquid phase neutrals.

"Solid support" refers to a solid material which can be derivatized with, or otherwise attached to, a capture reagent. Exemplary solid supports include probes, microtiter plates and chromatographic resins.

"Probe" in the context of this invention refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A "probe" will generally comprise a solid substrate (either flexible or rigid) comprising a sample presenting surface on which an analyte is presented to the source of ionizing energy.

"Surface-enhanced laser desorption/ionization" or "SELDI" refers to a method of desorption/ionization gas phase ion spectrometry (e.g., mass spectrometry) in which the analyte is captured on the surface of a SELDI probe that engages the probe interface of the gas phase ion spectrometer. In "SELDI MS," the gas phase ion spectrometer is a mass spectrometer. SELDI technology is described in, e.g., U.S. Pat. No. 5,719,060 (Hutchens and Yip) and U.S. Pat. No. 6,225,047 (Hutchens and Yip).

"Surface-Enhanced Affinity Capture" or "SEAC" is a version of SELDI that involves the use of probes comprising an absorbent surface (a "SEAC probe"). "Adsorbent surface" refers to a surface to which is bound an adsorbent (also called a "capture reagent" or an "affinity reagent"). An adsorbent is any material capable of binding an analyte (e.g., a target polypeptide or nucleic acid). "Chromatographic adsorbent" refers to a material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents). "Biospecific adsorbent" refers an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047 (Hutchens and Yip, "Use of retentate chromatography to generate difference maps," May 1, 2001).

In some embodiments, a SEAC probe is provided as a pre-activated surface which can be modified to provide an adsorbent of choice. For example, certain probes are provided with a reactive moiety that is capable of binding a biological molecule through a covalent bond. Epoxide and carbodiimidizole are useful reactive moieties to covalently bind biospecific adsorbents such as antibodies or cellular receptors.

"Adsorption" refers to detectable non-covalent binding of an analyte to an adsorbent or capture reagent.

"Surface-Enhanced Neat Desorption" or "SEND" is a version of SELDI that involves the use of probes comprising energy absorbing molecules chemically bound to the probe surface. ("SEND probe.") "Energy absorbing molecules" ("EAM") refer to molecules that are capable of absorbing energy from a laser desorption/ionization source and thereafter contributing to desorption and ionization of analyte molecules in contact therewith. The phrase includes molecules used in MALDI, frequently referred to as "matrix", and explicitly includes cinnamic acid derivatives, sinapinic acid ("SPA"), cyano-hydroxy-cinnamic acid ("CHCA") and dihydroxybenzoic acid, ferulic acid, hydroxyacetophenone derivatives, as well as others. It also includes EAMs used in SELDI. SEND is further described in U.S. Pat. No. 5,719,060 and U.S. patent application 60/408,255, filed Sep. 4, 2002 (Kitagawa, "Monomers And Polymers Having Energy Absorbing Moieties Of Use In Desorption/Ionization Of Analytes").

"Surface-Enhanced Photolabile Attachment and Release" or "SEPAR" is a version of SELDI that involves the use of probes having moieties attached to the surface that can covalently bind an analyte, and then release the analyte through breaking a photolabile bond in the moiety after exposure to light, e.g., laser light. SEPAR is further described in U.S. Pat. No. 5,719,060.

"Eluant" or "wash solution" refers to an agent, typically a solution, which is used to affect or modify adsorption of an analyte to an adsorbent surface and/or remove unbound materials from the surface. The elution characteristics of an eluant can depend on, for example, pH, ionic strength, hydrophobicity, degree of chaotropism, detergent strength and temperature.

"Analyte" refers to any component of a sample that is desired to be detected. The term can refer to a single component or a plurality of components in the sample.

The "complexity" of a sample adsorbed to an adsorption surface of an affinity capture probe means the number of different protein species that are adsorbed.

"Molecular binding partners" and "specific binding partners" refer to pairs of molecules, typically pairs of biomolecules that exhibit specific binding. Molecular binding partners include, without limitation, receptor and ligand, antibody and antigen, biotin and avidin, and biotin and streptavidin.

"Monitoring" refers to recording changes in a continuously varying parameter.

"Biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface, and therefore, function as probes.

"Protein biochip" refers to a biochip adapted for the capture of polypeptides. Many protein biochips are described in the art. These include, for example, protein biochips produced by Ciphergen Biosystems (Fremont, Calif.), Packard BioScience Company (Meriden Conn.), Zyomyvx (Hayward, Calif.) and Phylos (Lexington, Mass.). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001) and International publication WO 00/56934 (Englert et al., "Continuous porous matrix arrays," Sep. 28, 2000).

Protein biochips produced by Ciphergen Biosystems comprise surfaces having chromatographic or biospecific adsorbents attached thereto at addressable locations. Ciphergen ProteinChip® arrays include NP20, H4, H50, SAX-2, WCX-2, CM-10, IMAC-3, IMAC-30, LSAX-30, LWCX-30, IMAC-40, PS-10, PS-20 and PG-20. These protein biochips comprise an aluminum substrate in the form of a strip. The surface of the strip is coated with silicon dioxide.

In the case of the NP-20 biochip, silicon oxide functions as a hydrophilic adsorbent to capture hydrophilic proteins.

H4, H50, SAX-2, WCX-2, CM-10, IMAC-3, IMAC-30, PS-10 and PS-20 biochips further comprise a functionalized, cross-linked polymer in the form of a hydrogel physically attached to the surface of the biochip or covalently attached through a silane to the surface of the biochip. The H4 biochip has isopropyl functionalities for hydrophobic binding. The H50 biochip has nonylphenoxy-poly(ethylene glycol)methacrylate for hydrophobic binding. The SAX-2 biochip has quaternary ammonium functionalities for anion exchange. The WCX-2 and CM-10 biochips have carboxylate functionalities for cation exchange. The IMAC-3 and IMAC-30 biochips have nitriloacetic acid functionalities that adsorb transition metal ions, such as Cu++ and Ni++, by chelation. These immobilized metal ions allow adsorption of peptide and proteins by coordinate bonding. The PS-10 biochip has carboimidizole functional groups that can react with groups on proteins for covalent binding. The PS-20 biochip has epoxide functional groups for covalent binding with proteins. The PS-series biochips are useful for binding biospecific adsorbents, such as antibodies, receptors, lectins, heparin, Protein A, biotin/streptavidin and the like, to chip surfaces where they function to specifically capture analytes from a sample. The PG-20 biochip is a PS-20 chip to which Protein G is attached. The LSAX-30 (anion exchange), LWCX-30 (cation exchange) and IMAC-40 (metal chelate) biochips have functionalized latex beads on their surfaces. Such biochips are further described in: WO 00/66265 (Rich et al., "Probes for a Gas Phase Ion Spectrometer," Nov. 9, 2000); WO 00/67293 (Beecher et al., "Sample Holder with Hydrophobic Coating for Gas Phase Mass Spectrometer," Nov. 9, 2000); U.S. patent application US20030032043A1 (Pohl and Papanu, "Latex Based Adsorbent Chip," Jul. 16, 2002) and U.S. patent application 60/350,110 (Um et al., "Hydrophobic Surface Chip," Nov. 8, 2001).

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

"Marker" or "biomarker" in the context of the present invention refer to a polypeptide (of a particular apparent molecular weight), which is differentially present in a sample taken from subjects having human colorectal cancer as compared to a comparable sample taken from control subjects (e.g., a person with a negative diagnosis or undetectable colorectal cancer, normal or healthy subject). The term "biomarker" is used interchangeably with the term "marker." The biomarkers are identified by molecular mass in Daltons, and include the masses centered around the identified molecular masses for each marker.

The term "measuring" means methods which include detecting the presence or absence of marker(s) in the sample, quantifying the amount of marker(s) in the sample, and/or qualifying the type of biomarker. Measuring can be accomplished by methods known in the art and those further described herein, including but not limited to SELDI and immunoassay. Any suitable methods can be used to detect and measure one or more of the markers described herein. These methods include, without limitation, mass spectrometry (e.g., laser desorption/ionization mass spectrometry), fluorescence (e.g. sandwich immunoassay), surface plasmon resonance, ellipsometry and atomic force microscopy.

"Detect" refers to identifying the presence, absence or amount of the object to be detected.

The phrase "differentially present" refers to differences in the quantity and/or the frequency of a marker present in a sample taken from subjects having human cancer as compared to a control subject. For example, some markers described herein are present at an elevated level in samples of subjects compared to samples from control subjects. In contrast, other markers described herein are present at a decreased level in samples of colorectal cancer subjects compared to samples from control subjects. Furthermore, a marker can be a polypeptide, which is detected at a higher frequency or at a lower frequency in samples of human cancer subjects compared to samples of control subjects. A marker can be differentially present in terms of quantity, frequency or both.

A polypeptide is differentially present between two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between two sets of samples if the frequency of detecting the polypeptide in the cancer subjects' samples is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

"Diagnostic" means identifying the presence or nature of a pathologic condition, i.e., colorectal cancer. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., μg/ml) or a relative amount (e.g., relative intensity of signals).

A "diagnostic amount" of a marker refers to an amount of a marker in a subject's sample that is consistent with a diagnosis of colorectal cancer. A diagnostic amount can be either in absolute amount (e.g., μg/ml) or a relative amount (e.g., relative intensity of signals).

A "control amount" of a marker can be any amount or a range of amount, which is to be compared against a test amount of a marker. For example, a control amount of a marker can be the amount of a marker in a person without colorectal cancer. A control amount can be either in absolute amount (e.g., μg/ml) or a relative amount (e.g., relative intensity of signals).

As used herein, the term "sensitivity" is the percentage of subjects with a particular disease. For example, in the colorectal cancer group, the biomarkers of the invention have a sensitivity of about 80.0%-98.6%, and preferably a sensitivity of 85%, 87.5%, 90%, 92.5%, 95%, 97%, 98%, 990% or approaching 100%.

As used herein, the term "specificity" is the percentage of subjects correctly identified as having a particular disease i.e., normal or healthy subjects. For example, the specificity is calculated as the number of subjects with a particular disease as compared to non-cancer subjects (e.g., normal healthy subjects). The specificity of the assays described herein may range from about 80% to 100%. Preferably the specificity is about 90%, 95%, or 100%.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Immunoassay" is an assay that uses an antibody to specifically bind an antigen (e.g., a marker). The immunoassay is characterized by the use of specific binding properties of a particular antibody to isolate, target, and/or quantify the antigen.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well-characterized fragments produced by digestion with various peptidases. This includes, e.g., Fab" and F(ab)"$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g. Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

"Managing subject treatment" refers to the behavior of the clinician or physician subsequent to the determination of cancer status. For example, if the result of the methods of the present invention is inconclusive or there is reason that confirmation of status is necessary, the physician may order more tests. Alternatively, if the status indicates that treatment is appropriate, the physician may schedule the patient for treatment, e.g., surgery, administer one or more therapeutic agents or radiation. Likewise, if the status is negative, e.g., late stage colorectal cancer or if the status is acute, no further action may be warranted. Furthermore, if the results show that treatment has been successful, a maintenance therapy or no further management may be necessary.

DETAILED DESCRIPTION

The present invention provides biomarkers generated from comparison of protein profiles from subjects diagnosed with colorectal cancer and from subjects without known neoplastic diseases, using the mass spectrometry techniques. In particular, the invention provides that these biomarkers, used individually, or preferably in combination with other biomarkers from this group or with other diagnostic tests, provide a novel method of determining colorectal cancer status in a subject.

The present invention presents markers that are differentially present in samples of colorectal cancer subjects and control subjects, and the application of this discovery in methods and kits for determining colorectal cancer status. These protein markers are found in samples from colorectal cancer subjects at levels that are different than the levels in samples from subject in whom human cancer is undetectable. Accordingly, the amount of one or more markers found in a test sample compared to a control, or the presence or absence of one or more markers in the test sample provides useful information regarding the colorectal cancer status of the patient.

The present invention also relates to a method for identification of biomarkers for cancer, with high specificity and sensitivity. In particular, a panel of biomarkers were identified that are associated with colorectal cancer disease status.

In the data presented herein, we describe for the first time a serum protein profile which aids in the diagnosis of colorectal cancer. Examining 139 samples of subjects and healthy persons, this profile distinguished subjects with colorectal cancer from control subjects independent validation sets.

The protein profiles were robustly accurate (e.g., having a negative predictive value of about 94.4±%, a sensitivity of about 96.7%, and a specificity and positive predictive value of about 100%) in all examined serum sample sets and may therefore support the making of the diagnosis in subjects.

Due to their high sensitivity ranging between about 80% and about 99%, for example, 96.7%, the "colorectal cancer-sensitive" serum protein profiles lend themselves to support the decision making process for treatment.

The previous standard for protein profiling has been two-dimensional gel electrophoresis. That approach is very laborious, difficult to automate, has a significantly limited sample capacity as well as a limited detection of low-abundant proteins and proteins below 10,000 Dalton (Griffin, 2001). We show that highly standardized and semi-automated SELDI-TOF MS of fractionated serum is suitable to generate reproducible serum protein profiles in large-scale studies. Our serum protein profile represents a novel and non-invasive diagnostic tool requiring less than 100 μl serum.

Description of the Biomarkers

The corresponding proteins or fragments of proteins for these biomarkers are represented as intensity peaks in SELDI (surface enhanced laser desorption/ionization) protein chip/mass spectra with molecular masses centered around the values indicated as follows.

Biomarkers from the whole serum fraction include the biomarkers identified as: Markers I-XIV, described herein.

These masses for Markers I-XIV are considered accurate to within 0.15 percent of the specified value as determined by the disclosed SELDI-mass spectroscopy protocol.

As discussed above, Markers I-XIV also may be characterized based on affinity for an adsorbent, particularly binding to a cation-exchange or hydrophobic surface under the conditions specified in the Examples, which follow.

The above-identified biomarkers, are examples of biomarkers, as determined by molecular weights, identified by the methods of the invention and serve merely as an illustrative example and are not meant to limit the invention in any way.

A major advantage of identification of these markers is their high specificity and ability to differentiate between different colorectal cancer disease states (e.g., between different colorectal cancer subtypes).

More specifically, the present invention is based upon the discovery of protein markers that are differentially present in samples of human colorectal cancer subjects and control subjects, and the application of this discovery in methods and kits for aiding a human colorectal cancer diagnosis. Some of these protein markers are found at an elevated level and/or more frequently in samples from human colorectal cancer subjects compared to a control (e.g., subjects with diseases other than colorectal cancer). Accordingly, the amount of one or more markers found in a test sample compared to a control, or the mere detection of one or more markers in the test sample provides useful information regarding probability of whether a subject being tested has colorectal cancer or not, and/or whether a subject being tested has a particular colorectal cancer subtype or not.

The protein markers of the present invention have a number of other uses. For example, the markers can be used to screen for compounds that modulate the expression of the markers in vitro or in vivo, which compounds in turn may be useful in treating or preventing human colorectal cancer in subjects. In another example, markers can be used to monitor responses to certain treatments of human colorectal cancer. In yet another example, the markers can be used in heredity studies. For instance, certain markers may be genetically linked. This can be determined by, e.g., analyzing samples from a population of human colorectal cancer subjects whose families have a history of colorectal cancer. The results can then be compared with data obtained from, e.g., colorectal cancer subjects whose families do not have a history of colorectal cancer. The markers that are genetically linked may be used as a tool to determine if a subject whose family has a history of colorectal cancer is pre-disposed to having colorectal cancer.

In another aspect, the invention provides methods for detecting markers which are differentially present in the samples of an colorectal cancer patient and a control (e.g., subjects in non-colorectal cancer subjects). The markers can be detected in a number of biological samples. The sample is preferably a biological fluid sample. Examples of a biological fluid sample useful in this invention include blood, blood serum, plasma, urine, tears, saliva, nipple aspirate, cerebrospinal fluid, etc. Because all of the markers are found in blood serum, blood serum is a preferred sample source for embodiments of the invention.

Any suitable methods can be used to detect one or more of the markers described herein. These methods include, without limitation, mass spectrometry (e.g., laser desorption/ionization mass spectrometry), fluorescence (e.g. sandwich immunoassay), surface plasmon resonance, ellipsometry and atomic force microscopy. Methods may further include, by one or more of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS).sub.n, quadrupole mass spectrometry, fourier transform mass spectrometry (FTMS), and ion trap mass spectrometry, where n is an integer greater than zero.

The following example is illustrative of the methods used to identify biomarkers for detection of colorectal cancer. It is not meant to limit or construe the invention in any way. A sample, such as for example, serum from a subject or patient, is immobilized on a biochip. Preferably, the biochip comprises a functionalized, cross-linked polymer in the form of a hydrogel physically attached to the surface of the biochip or covalently attached through a silane to the surface of the biochip. However, any biochip which can bind samples from subjects can be used. The surfaces of the biochips are comprised of, for example, hydrophilic adsorbent to capture hydrophilic proteins (e.g. silicon oxide); carboimidizole functional groups that can react with groups on proteins for covalent binding; epoxide functional groups for covalent binding with proteins (e.g. antibodies, receptors, lectins, heparin, Protein A, biotin/streptavidin and the like); anionic exchange groups; cation exchange groups; metal chelators and the like.

Preferably, samples are pre-fractionated prior to immobilization as discussed below. Analytes or samples captured on the surface of a biochip can be detected by any method known in the art. This includes, for example, mass spectrometry, fluorescence, surface plasmon resonance, ellipsometry and atomic force microscopy. Mass spectrometry, and particularly SELDI mass spectrometry, is a particularly useful method for detection of the biomarkers of this invention. Other methods include, chemical extraction partitioning, ion exchange chromatography, reverse phase liquid chromatography, isoelectric focusing, one-dimensional polyacrylamide gel electrophoresis (PAGE), two-dimensional polyacrylamide gel electrophoresis (2D-PAGE), thin-layer chromatography, gas chromatography, liquid chromatography, and any combination thereof.

Immobilized samples or analytes are preferably subjected to laser ionization and the intensity of signal for mass/charge ratio is detected. The data obtained from the mass/charge ratio signal is transformed into data which is read by any type of computer. An algorithm is executed by the computer user that classifies the data according to user input parameters for detecting signals that represent biomarkers present in, for example, colorectal cancer subjects and are lacking in non-colorectal cancer subject controls. The biomarkers are most preferably identified by their molecular weights.

Test Samples

Subject Types

Samples are collected from subjects who want to establish colorectal cancer-status. The subjects may be subjects who have been determined to have a high risk of colorectal cancer based on their family history, a previous chemotherapeutic treatment, subjects with physical symptoms known to be associated with colorectal cancer, subjects identified through screening assays (e.g., fecal occult blood testing or sigmoidoscopy) or rectal digital exam or rigid or flexible colonoscopy or CT scan or other x-ray techniques. Other subjects include subjects who have colorectal cancer and the test is being used to determine the effectiveness of therapy or treatment they are receiving. Also, subjects could include healthy people who are having a test as part of a routine examination, or to establish baseline levels of the biomarkers. Samples may be collected from people who had been diagnosed with colorectal cancer and received treatment to eliminate the colorectal cancer, or perhaps are in remission.

Types of Sample and Preparation of the Sample

The markers can be measured in different types of biological samples. The sample is preferably a biological fluid sample. Examples of a biological fluid sample useful in this invention include blood, blood serum, plasma, vaginal secretions, urine, tears, saliva, urine, tissue, cells, organs, seminal fluids, bone marrow, cerebrospinal fluid, etc. Because all of the markers are found in blood serum, blood serum is a preferred sample source for embodiments of the invention.

If desired, the sample can be prepared to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography, affinity chromatography (e.g., with antibodies) and the like. The method of fractionation depends on the type of detection method used. Any method that enriches for the protein of interest can be used. Typically, preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis.

In one embodiment, a sample can be pre-fractionated according to size of proteins in a sample using size exclusion chromatography. For a biological sample wherein the amount of sample available is small, preferably a size selection spin column is used. For example, a K30 spin column (available from Princeton Separation, Ciphergen Biosystems, Inc., etc.) can be used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins; and so on. Each fraction can then be analyzed by gas phase ion spectrometry for the detection of markers.

In another embodiment, a sample can be pre-fractionated by anion exchange chromatography. In yet another embodiment, a sample can be pre-fractionated by heparin chromatography.

In yet another embodiment, a sample can be pre-fractionated by removing proteins that are present in a high quantity or that may interfere with the detection of markers in a sample. For example, in a blood serum sample, serum albumin is present in a high quantity and may obscure the analysis of markers. Thus, a blood serum sample can be pre-fractionated by removing serum albumin. Serum albumin can be removed using a substrate that comprises adsorbents that specifically bind serum albumin. For example, a column which comprises, e.g., Cibacron blue agarose (which has a high affinity for serum albumin) or anti-serum albumin antibodies can be used. In yet another embodiment, a sample can be pre-fractionated by isolating proteins that have a specific characteristic, e.g. are glycosylated. For example, a blood serum sample can be fractionated by passing the sample over a lectin chromatography column (which has a high affinity for sugars).

Many types of affinity adsorbents exist which are suitable for pre-fractionating blood serum samples. An example of one other type of affinity chromatography available to pre-fractionate a sample is a single stranded DNA spin column. These columns bind proteins which are basic or positively charged. Bound proteins are then eluted from the column using eluants containing denaturants or high pH.

Thus there are many ways to reduce the complexity of a sample based on the binding properties of the proteins in the sample, or the characteristics of the proteins in the sample.

In yet another embodiment, a sample can be fractionated using a sequential extraction protocol. In sequential extraction, a sample is exposed to a series of adsorbents to extract different types of biomolecules from a sample. For example, a sample is applied to a first adsorbent to extract certain proteins, and an eluant containing non-adsorbent proteins (i.e., proteins that did not bind to the first adsorbent) is collected. Then, the fraction is exposed to a second adsorbent. This further extracts various proteins from the fraction. This second fraction is then exposed to a third adsorbent, and so on.

Any suitable materials and methods can be used to perform sequential extraction of a sample. For example, a series of spin columns comprising different adsorbents can be used. In another example, a multi-well comprising different adsorbents at its bottom can be used. In another example, sequential extraction can be performed on a probe adapted for use in a gas phase ion spectrometer, wherein the probe surface comprises adsorbents for binding biomolecules.

In yet another embodiment, biomolecules in a sample can be separated by high-resolution electrophoresis, e.g., one or two-dimensional gel electrophoresis. A fraction containing a marker can be isolated and further analyzed by gas phase ion spectrometry. Preferably, two-dimensional gel electrophoresis is used to generate two-dimensional array of spots of biomolecules, including one or more markers. See, e.g., Jungblut and Thiede, *Mass Spectr. Rev.* 16:145-162 (1997).

The two-dimensional gel electrophoresis can be performed using methods known in the art. See, e.g., Deutscher ed., *Methods In Enzymology* vol. 182. Typically, biomolecules in a sample are separated by, e.g., isoelectric focusing, during which biomolecules in a sample are separated in a pH gradient until they reach a spot where their net charge is zero (i.e., isoelectric point). This first separation step results in one-dimensional array of biomolecules. The biomolecules in one-dimensional array is further separated using a technique generally distinct from that used in the first separation step.

Biomolecules in the two-dimensional array can be detected using any suitable methods known in the art. For example, biomolecules in a gel can be labeled or stained (e.g., Coomassie Blue or silver staining). If gel electrophoresis generates spots that correspond to the molecular weight of one or more markers of the invention, the spot can be is further analyzed by gas phase ion spectrometry. For example, spots can be excised from the gel and analyzed by gas phase ion spectrometry. Alternatively, the gel containing biomolecules can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI (e.g., using ProteinChip® array) as described in detail below.

Prior to gas phase ion spectrometry analysis, it may be desirable to cleave biomolecules in the spot into smaller fragments using cleaving reagents, such as proteases (e.g., trypsin). The digestion of biomolecules into small fragments provides a mass fingerprint of the biomolecules in the spot, which can be used to determine the identity of markers if desired.

In yet another embodiment, high performance liquid chromatography (HPLC) can-be used to separate a mixture of biomolecules in a sample based on their different physical properties, such as polarity, charge and size. HPLC instruments typically consist of a reservoir of mobile phase, a pump, an injector, a separation column, and a detector. Biomolecules in a sample are separated by injecting an aliquot of the sample onto the column. Different biomolecules in the mixture pass through the column at different rates due to differences in their partitioning behavior between the mobile liquid phase and the stationary phase. A fraction that corresponds to the molecular weight and/or physical properties of one or more markers can be collected. The fraction can then be analyzed by gas phase ion spectrometry to detect markers. For example, the spots can be analyzed using either MALDI or SELDI (e.g., using ProteinChip® array) as described in detail below.

Optionally, a marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because smaller markers are more easily resolved by mass spectrometry.

Capture of Markers

Biomarkers are preferably captured with capture reagents immobilized to a solid support, such as any biochip described herein, a multiwell microtiter plate, a resin, or nitrocellulose membranes that are subsequently probed for the presence of proteins. In particular, the biomarkers of this invention are preferably captured on SELDI protein biochips. Capture can be on a chromatographic surface or a biospecific surface. Any of the SELDI protein biochips comprising reactive surfaces can be used to capture and detect the biomarkers of this invention. However, the biomarkers of this invention bind well to cation-exchange or hydrophobic surfaces. The IMAC3 or WCX2 biochips are the preferred SELDI biochips for capturing the biomarkers of this invention. Any of the SELDI protein biochips comprising reactive surfaces can be used to capture and detect the biomarkers of this invention. These biochips can be derivatized with the antibodies that specifically capture the biomarkers, or they can be derivatized with capture reagents, such as protein A or protein G that bind immunoglobulins. Then the biomarkers can be captured in solution using specific antibodies and the captured markers isolated on chip through the capture reagent.

In general, a sample containing the biomarkers, such as serum, is placed on the active surface of a biochip for a sufficient time to allow binding. Then, unbound molecules are washed from the surface using a suitable eluant, such as phosphate buffered saline. In general, the more stringent the eluant, the more tightly the proteins must be bound to be retained after the wash. The retained protein biomarkers now can be detected by appropriate means.

Detection and Measurement of Markers

Once captured on a substrate, e.g., biochip or antibody, any suitable method can be used to measure a marker or markers in a sample. For example, markers can be detected and/or measured by a variety of detection methods including for example, gas phase ion spectrometry methods, optical methods, electrochemical methods, atomic force microscopy, radio frequency methods, surface plasmon resonance, ellipsometry and atomic force microscopy.

SELDI

One preferred method of detection and/or measurement of the biomarkers uses mass spectrometry, and in particular, "Surface-enhanced laser desorption/ionization" or "SELDI". SELDI refers to a method of desorption/ionization gas phase ion spectrometry (e.g., mass spectrometry) in which the analyte is captured on the surface of a SELDI probe that engages the probe interface. In "SELDI MS," the gas phase ion spectrometer is a mass spectrometer. SELDI technology is described in more detail above and as follows.

Preferably, a laser desorption time-of-flight mass spectrometer is used in embodiments of the invention. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Markers on the substrate surface can be desorbed and ionized using gas phase ion spectrometry. Any suitable gas phase ion spectrometers can be used as long as it allows markers on the substrate to be resolved. Preferably, gas phase ion spectrometers allow quantitation of markers.

In one embodiment, a gas phase ion spectrometer is a mass spectrometer. In a typical mass spectrometer, a substrate or a probe comprising markers on its surface is introduced into an inlet system of the mass spectrometer. The markers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions.

Preferably, a laser desorption time-of-flight mass spectrometer is used in embodiments of the invention. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

In another embodiment, an ion mobility spectrometer can be used to detect markers. The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector which can then be used to identify a marker or other substances in a sample. One advantage of ion mobility spectrometry is that it can operate at atmospheric pressure.

In yet another embodiment, a total ion current measuring device can be used to detect and characterize markers. This device can be used when the substrate has a only a single type of marker. When a single type of marker is on the substrate, the total current generated from the ionized marker reflects the quantity and other characteristics of the marker. The total ion current produced by the marker can then be compared to a control (e.g., a total ion current of a known compound). The quantity or other characteristics of the marker can then be determined.

Immunoassay

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

An immunoassay is an assay that uses an antibody to specifically bind an antigen (e.g., a marker). The immunoassay is characterized by the use of specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein.

Using the purified markers or their nucleic acid sequences, antibodies that specifically bind to a marker can be prepared using any suitable methods known in the art. See, e.g., Coligan, *Current Protocols in Immunology* (1991); Harlow & Lane, Antibodies: *A Laboratory Manual* (1988); Goding, *Monoclonal Antibodies: Principles and Practice* (2d ed. 1986); and Kohler & Milstein, *Nature* 256:495-497 (1975). Such techniques include, but are not limited to, antibody preparation by selection of antibodies from libraries of recombinant antibodies in phage or similar vectors, as well as preparation of polygonal and monoclonal antibodies by immunizing rabbits or mice (see, e.g., Huse et al., *Science* 246:1275-1281 (1989); Ward et al., *Nature* 341:544-546 (1989)). Typically a specific or selective reaction will be at least twice background signal or noise and more typically more than 10 to 100 times background.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array described above. The sample is preferably a biological fluid sample taken from a subject. Examples of biological fluid samples include blood, serum, plasma, nipple aspirate, urine, tears, saliva etc. In a preferred embodiment, the biological fluid comprises blood serum. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Methods for measuring the amount of, or presence of, antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., *Methods in Cell Biology: Antibodies in Cell Biology*, volume 37 (Asai, ed. 1993); *Basic and Clinical Immunology* (Stites & Terr, eds., 7th ed. 1991); and Harlow & Lane, supra.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Immunoassays can be used to determine presence or absence of a marker in a sample as well as the quantity of a marker in a sample. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid humancolorectal cancer diagnosis or prognosis. In another example, the methods for detection of the markers can be used to monitor responses in a subject to colorectal cancer treatment. In another example, the methods for detecting markers can be used to assay for and to identify compounds that modulate expression of these markers in vivo or in vitro. In a preferred example, the biomarkers are used to differentiate between the different stages of tumor progression, thus aiding in determining appropriate treatment and extent of metastasis of the tumor.

Use of Modified Forms of a Biomarker

It has been found that proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. The collection of proteins including a specific protein and all modified forms of it is referred to herein as a "protein cluster." The collection of all modified forms of a specific protein, excluding the specific protein, itself, is referred to herein as a "modified protein cluster." Modified forms of any biomarker of this invention (including any of Markers I through XIV) also may be used, themselves, as biomarkers. In certain cases the modified forms may exhibit better discriminatory power in diagnosis than the specific forms set forth herein.

Modified forms of a biomarker including any of Markers I through XIV can be initially detected by any methodology that can detect and distinguish the modified from the biomarker. A preferred method for initial detection involves first capturing the biomarker and modified forms of it, e.g., with biospecific capture reagents, and then detecting the captured proteins by mass spectrometry. More specifically, the proteins are captured using biospecific capture reagents, such as antibodies, aptamers or Affibodies that recognize the biomarker and modified forms of it. This method also will also result in the capture of protein interactors that are bound to the proteins or that are otherwise recognized by antibodies and that, themselves, can be biomarkers. Preferably, the biospecific capture reagents are bound to a solid phase. Then, the captured proteins can be detected by SELDI mass spectrometry or by eluting the proteins from the capture reagent and detecting the eluted proteins by traditional MALDI or by SELDI. The use of mass spectrometry is especially attractive because it can distinguish and quantify modified forms of a protein based on mass and without the need for labeling.

Preferably, the biospecific capture reagent is bound to a solid phase, such as a bead, a plate, a membrane or a chip. Methods of coupling biomolecules, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different target proteins can be mixed in the same place, or they can be attached to solid phases in different physical or addressable locations. For example, one can load multiple columns with derivatized beads, each column able to capture a single protein cluster. Alternatively, one can pack a single column with different beads derivatized with capture reagents against a variety of protein clusters, thereby capturing all the analytes in a single place. Accordingly, antibody-derivatized bead-based technologies, such as xMAP technology of Luminex (Austin, Tex.) can be used to detect the protein clusters. However, the biospecific capture reagents must be specifically directed toward the members of a cluster in order to differentiate them.

In yet another embodiment, the surfaces of biochips can be derivatized with the capture reagents directed against protein clusters either in the same location or in physically different addressable locations. One advantage of capturing different clusters in different addressable locations is that the analysis becomes simpler.

After identification of modified forms of a protein and correlation with the clinical parameter of interest, the modified form can be used as a biomarker in any of the methods of this invention. At this point, detection of the modified from can be accomplished by any specific detection methodology including affinity capture followed by mass spectrometry, or traditional immunoassay directed specifically the modified form. Immunoassay requires biospecific capture reagents, such as antibodies, to capture the analytes. Furthermore, if the assay must be designed to specifically distinguish protein and modified forms of protein. This can be done, for example, by employing a sandwich assay in which one antibody captures more than one form and second, distinctly labeled antibodies, specifically bind, and provide distinct detection of, the various forms. Antibodies can be produced by immunizing animals with the biomolecules. This invention contemplates traditional immunoassays including, for example, sandwich immunoassays including ELISA or fluorescence-based immunoassays, as well as other enzyme immunoassays.

Data Analysis

The methods for detecting these markers in a sample have many applications. For example, one or more markers can be measured to aid human colorectal cancer diagnosis or prognosis. In another example, the methods for detection of the markers can be used to monitor responses in a subject to colorectal cancer treatment. In another example, the methods for detecting markers can be used to assay for and to identify compounds that modulate expression of these markers in vivo or in vitro.

Differentiation of non-colorectal cancer and colorectal cancer status may be by the detection of one or more of the Markers listed in Table 1. For example, an exemplary marker that may independently discriminate between colorectal and non-colorectal status is Marker X: 9148.7. Combinations of markers are also useful in the methods of the invention for the discrimination of on-colorectal cancer and colorectal cancer status, for example, Marker IV: 5715.9 and Marker X: 9148.7; Marker X: 9148.7 and Marker XI: 9556.6; Marker II: 2591.1, Marker X: 9148.7, and Marker XII: 14653.8; Marker VI: 7568.9, Marker X: 9148.7, and Marker XII: 14653.8; Marker VII: 7683.6, Marker X: 9148.7, and Marker XII: 14653.8; Marker IX: 7905.8, Marker X: 9148.7, Marker I: 2172.8, and Marker III: 2646.9; Marker V: 7005.2, Marker VIII: 7722.6, Marker X: 9148.7, Marker XIII: 14698, and Marker III: 2646.9; Marker V: 7005.2, Marker IX: 7905.8, Marker X: 9148.7, Marker XII: 14653.8, and Marker III: 2646.9; and/or Marker I: 2172.8, Marker II: 2591.1, Marker III: 2646.9, Marker IV: 5715.9, Marker V: 7005.2, Marker VI: 7568.9, Marker VII: 7683.6, Marker VIII: 7722.6, Marker IX: 7905.8, Marker X: 9148.7, Marker XI: 9556.6, Marker XII: 14653.8, and Marker XIII: 14698.6.

Data generated by desorption and detection of markers can be analyzed using any suitable means. In one embodiment, data is analyzed with the use of a programmable digital computer. The computer program generally contains a readable medium that stores codes. Certain code can be devoted to memory that includes the location of each feature on a probe, the identity of the adsorbent at that feature and the elution conditions used to wash the adsorbent. The computer also contains code that receives as input, data on the strength of the signal at various molecular masses received from a particular addressable location on the probe. This data can indicate the number of markers detected, including the strength of the signal generated by each marker.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each marker or other biomolecules can be displayed in the form of relative intensities in the scale desired (e.g., 100). Alternatively, a standard (e.g., a serum protein) may be admitted with the sample so that a peak from the standard can be used as a reference to calculate relative intensities of the signals observed for each marker or other markers detected.

The computer can transform the resulting data into various formats for displaying. In one format, referred to as "spectrum view or retentate map," a standard spectral view can be displayed, wherein the view depicts the quantity of marker reaching the detector at each particular molecular weight. In another format, referred to as "peak map," only the peak height and mass information are retained from the spectrum view, yielding a cleaner image and enabling markers with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique markers and markers which are up- or down-regulated between samples. Marker profiles (spectra) from any two samples may be compared visually. In yet another format, Spotfire Scatter Plot can be used, wherein markers that are detected are plotted as a dot in a plot, wherein one axis of the plot represents the apparent molecular of the markers detected and another axis represents the signal intensity of markers detected. For each sample, markers that are detected and the amount of markers present in the sample can be saved in a computer readable medium. This data can then be compared to a control (e.g., a profile or quantity of markers detected in control, e.g., men in whom human colorectal cancer is undetectable).

When the sample is measured and data is generated, e.g., by mass spectrometry, the data is then analyzed by a computer software program. Generally, the software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" and human cancer and determines the closeness of fit between the two signals. The software also can include code indicating which the test sample is closest to, thereby providing a probable diagnosis.

In preferred methods of the present invention, multiple biomarkers are measured. The use of multiple biomarkers increases the predictive value of the test and provides greater utility in diagnosis, toxicology, patient stratification and patient monitoring. The process called "Pattern recognition" detects the patterns formed by multiple biomarkers greatly improves the sensitivity and specificity of clinical proteomics for predictive medicine. Subtle variations in data from clinical samples, e.g., obtained using SELDI, indicate that certain patterns of protein expression can predict phenotypes such as the presence or absence of a certain disease, a particular stage of cancer-progression, or a positive or adverse response to drug treatments.

Data generation in mass spectrometry begins with the detection of ions by an ion detector as described above. Ions that strike the detector generate an electric potential that is digitized by a high speed time-array recording device that digitally captures the analog signal. Ciphergen's Protein-Chip® system employs an analog-to-digital converter (ADC) to accomplish this. The ADC integrates detector output at regularly spaced time intervals into time-dependent bins. The time intervals typically are one to four nanoseconds long. Furthermore, the time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation, baseline subtraction, high frequency noise filtering.

TOF-to-M/Z transformation involves the application of an algorithm that transforms times-of-flight into mass-to-charge ratio (M/Z). In this step, the signals are converted from the time domain to the mass domain. That is, each time-of-flight is converted into mass-to-charge ratio, or M/Z. Calibration can be done internally or externally. In internal calibration, the sample analyzed contains one or more analytes of known M/Z. Signal peaks at times-of-flight representing these massed analytes are assigned the known M/Z. Based on these assigned M/Z ratios, parameters are calculated for a mathematical function that converts times-of-flight to M/Z. In external calibration, a function that converts times-of-flight to M/Z, such as one created by prior internal calibration, is applied to a time-of-flight spectrum without the use of internal calibrants.

Baseline subtraction improves data quantification by eliminating artificial, reproducible instrument offsets that perturb the spectrum. It involves calculating a spectrum baseline using an algorithm that incorporates parameters such as peak width, and then subtracting the baseline from the mass spectrum.

High frequency noise signals are eliminated by the application of a smoothing function. A typical smoothing function applies a moving average function to each time-dependent bin. In an improved version, the moving average filter is a variable width digital filter in which the bandwidth of the filter varies as a function of, e.g., peak bandwidth, generally becoming broader with increased time-of-flight. See, e.g., WO 00/70648, Nov. 23, 2000 (Gavin et al., "Variable Width Digital Filter for Time-of-flight Mass Spectrometry").

Analysis generally involves the identification of peaks in the spectrum that represent signal from an analyte. Peak selection can, of course, be done by eye. However, software is available as part of Ciphergen's ProteinChip® software that can automate the detection of peaks. In general, this software functions by identifying signals having a signal-to-noise ratio above a selected threshold and labeling the mass of the peak at the centroid of the peak signal. In one useful application many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Peak data from one or more spectra can be subject to further analysis by, for example, creating a spreadsheet in which each row represents a particular mass spectrum, each column represents a peak in the spectra defined by mass, and each cell includes the intensity of the peak in that particular spectrum. Various statistical or pattern recognition approaches can applied to the data.

In one example, Ciphergen's Biomarker Patterns™ Software is used to detect a pattern in the spectra that are generated. The data is classified using a pattern recognition process that uses a classification model. In general, the spectra will represent samples from at least two different groups for which a classification algorithm is sought. For example, the groups can be pathological v. non-pathological (e.g., colorectal cancer v. non-colorectal cancer), drug responder v. drug non-responder, toxic response v. non-toxic response, progressor to disease state v. non-progressor to disease state, phenotypic condition present v. phenotypic condition absent.

The spectra that are generated in embodiments of the invention can be classified using a pattern recognition process that uses a classification model. In some embodiments, data derived from the spectra (e.g., mass spectra or time-of-flight spectra) that are generated using samples such as "known samples" can then be used to "train" a classification model. A "known sample" is a sample that is pre-classified (e.g., colorectal cancer or not colorectal cancer). Data derived from the spectra (e.g., mass spectra or time-of-flight spectra) that are generated using samples such as "known samples" can then be used to "train" a classification model. A "known sample" is a sample that is pre-classified. The data that are derived from the spectra and are used to form the classification model can be referred to as a "training data set". Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased vs. non diseased).

The training data set that is used to form the classification model may comprise raw data or pre-processed data. In some embodiments, raw data can be obtained directly from time-of-flight spectra or mass spectra, and then may be optionally "pre-processed" in any suitable manner. For example, signals above a predetermined signal-to-noise ratio can be selected so that a subset of peaks in a spectrum is selected, rather than selecting all peaks in a spectrum. In another example, a predetermined number of peak "clusters" at a common value (e.g., a particular time-of-flight value or mass-to-charge ratio value) can be used to select peaks. Illustratively, if a peak at a given mass-to-charge ratio is in less than 50% of the mass spectra in a group of mass spectra, then the peak at that mass-to-charge ratio can be omitted from the training data set. Pre-processing steps such as these can be used to reduce the amount of data that is used to train the classification model.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, which is herein incorporated by reference in its entirety.

In supervised classification, training data containing examples of known categories are presented to a learning mechanism, which learns one more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as backpropagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. 2002 0138208 A1 (Paulse et al., "Method for analyzing mass spectra," Sep. 26, 2002.

In other embodiments, the classification models that are created can be formed using unsupervised learning methods. Unsupervised classification attempts to learn classifications based on similarities in the training data set, without pre classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described in, for example, WO 01/31580 (Barnhill et al., "Methods and devices for identifying patterns in biological systems and methods of use thereof," May 3, 2001); U.S. 2002/0193950 A1 (Gavin et al., "Method or analyzing mass spectra," Dec. 19, 2002); U.S. 2003/0004402 A1 (Hitt et al., "Process for discriminating between biological states based on hidden patterns from biological data," Jan. 2, 2003); and U.S. 2003/0055615 A1 (Zhang and Zhang, "Systems and methods for processing biological expression data" Mar. 20, 2003).

More specifically, to obtain the biomarkers the peak intensity data of samples from subjects, e.g., cancer subjects, and healthy controls are used as a "discovery set." This data were combined and randomly divided into a training set and a test set to construct and test multivariate predictive models using a non-linear version of Unified Maximum Separability Analysis ("USMA") classifiers. Details of USMA classifiers are described in U.S. 2003/0055615 A1.

Generally, the data generated from Section IV above is inputted into a diagnostic algorithm (i.e., classification algorithm as described above). The classification algorithm is then generated based on the learning algorithm. The process involves developing an algorithm that can generate the classification algorithm. The methods of the present invention generate a more accurate classification algorithm by accessing a number of cancer and normal samples of a sufficient number based on statistical sample calculations. The samples are used as a training set of data on learning algorithm.

The generation of the classification, i.e., diagnostic, algorithm is dependent upon the assay protocol used to analyze samples and generate the data obtained in Section IV above. It is imperative that the protocol for the detection and/or measurement of the markers (e.g., in step IV) must be the same as that used to obtain the data used for developing the classification algorithm. The assay conditions, which must be maintained throughout the training and classification systems include chip type and mass spectrometer parameters, as well as general protocols for sample preparation and testing. If the protocol for the detection and/or measurement of the markers (step IV) is changed, the learning algorithm and classification algorithm must also change. Similarly, if the learning algorithm and classification algorithm change, then the protocol for the detection and/or measurement of markers (step IV) must also change to be consistent with that used to generate classification algorithm. Development of a new classification model would require accessing a sufficient number of cancer and normal samples, developing a new training set of data based on a new detection protocol, generating a new classification algorithm using the data and finally, verifying the classification algorithm with a multi-site study.

The classification models can be formed on and used on any suitable digital computer. Suitable digital computers include micro, mini, or large computers using any standard or specialized operating system such as a Unix, Windows™ or Linux™ based operating system. The digital computer that is used may be physically separate from the mass spectrometer that is used to create the spectra of interest, or it may be coupled to the mass spectrometer. If it is separate from the mass spectrometer, the data must be inputted into the computer by some other means, whether manually or automated. The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The invention provides methods for aiding a human colorectal cancer diagnosis using one or more markers, for example Markers in the tables and figures which follow, and including one or more Markers I through XIII as specified herein. These markers can be used alone, in combination with other markers in any set, or with entirely different markers in aiding human colorectal cancer diagnosis. The markers are differentially present in samples of a human colorectal cancer patient and a normal subject in whom human colorectal cancer is undetectable. For example, some of the markers are expressed at an elevated level and/or are present at a higher frequency in human colorectal cancer subjects than in normal subjects, while some of the markers are expressed at a decreased level and/or are present at a lower frequency in human colorectal cancer subjects than in normal subjects. Therefore, detection of one or more of these markers in a person would provide useful information regarding the probability that the person may have colorectal cancer.

In a preferred embodiment, a serum sample is collected from a patient and then either left unfractionated, or fractionated using an anion exchange resin as described above. The biomarkers in the sample are captured using an IMAC3 ProteinChip array or a WCX2 ProteinChip array. The markers are then detected using SELDI. The results are then entered into a computer system, which contains an algorithm that is designed using the same parameters that were used in the learning algorithm and classification algorithm to originally determine the biomarkers. The algorithm produces a diagnosis based upon the data received relating to each biomarker.

The diagnosis is determined by examining the data produced from the SELDI tests with the classification algorithm that is developed using the biomarkers. The classification algorithm depends on the particulars of the test protocol used to detect the biomarkers. These particulars include, for example, sample preparation, chip type and mass spectrometer parameters. If the test parameters change, the algorithm must change. Similarly, if the algorithm changes, the test protocol must change.

In another embodiment, the sample is collected from the patient. The biomarkers are captured using an antibody ProteinChip array as described above. The markers are detected using a biospecific SELDI test system. The results are then entered into a computer system, which contains an algorithm that is designed using the same parameters that were used in the learning algorithm and classification algorithm to originally determine the biomarkers. The algorithm produces a diagnosis based upon the data received relating to each biomarker.

In yet other preferred embodiments, the markers are captured and tested using non-SELDI formats. In one example, the sample is collected from the patient. The biomarkers are captured on a substrate using other known means, e.g., antibodies to the markers. The markers are detected using methods known in the art, e.g., optical methods and refractive index. Examples of optical methods include detection of fluorescence, e.g., ELISA. Examples of refractive index include surface plasmon resonance. The results for the markers are then subjected to an algorithm, which may or may not require artificial intelligence. The algorithm produces a diagnosis based upon the data received relating to each biomarker.

In any of the above methods, the data from the sample may be fed directly from the detection means into a computer containing the diagnostic algorithm. Alternatively, the data obtained can be fed manually, or via an automated means, into a separate computer that contains the diagnostic algorithm.

Accordingly, embodiments of the invention include methods for aiding a human colorectal cancer diagnosis, wherein the method comprises: (a) detecting at least one marker in a sample, wherein the marker is selected from any of the Markers I-XIV; and (b) correlating the detection of the marker or markers with a probable diagnosis of human colorectal cancer. The correlation may take into account the amount of the marker or markers in the sample compared to a control amount of the marker or markers (up or down regulation of the marker or markers) (e.g., in normal subjects in whom human colorectal cancer is undetectable). The correlation may take into account the presence or absence of the markers in a test sample and the frequency of detection of the same markers in a control. The correlation may take into account both of such factors to facilitate determination of whether a subject has a human colorectal cancer or not.

In a preferred embodiment, Markers I-XIV are used to make a correlation with colorectal cancer, wherein the colorectal cancer may be any subtype.

Any suitable samples can be obtained from a subject to detect markers. Preferably, a sample is a blood serum sample from the subject. If desired, the sample can be prepared as described above to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography and the like. Sample preparations, such as pre-fractionation protocols, are optional and may not be necessary to enhance detectability of markers depending on the methods of detection used. For example, sample preparation may be unnecessary if antibodies that specifically bind markers are used to detect the presence of markers in a sample.

Processes for the purification of a biomarker include fractioning a sample, as described herein, for example, by size-exclusion chromatography and collecting a fraction that includes one or more biomarkers; and/or fractionating a sample comprising the one or more biomarkers by anion exchange chromatography and collecting a fraction that includes one or more biomarkers, wherein the biomarker is selected from one or more of the biomarkers of Table 1.

A software product of the invention may be used to identify biomarkers. The software product would have an algorithm for determining distance dependant K nearest neighbors.

Method of the invention for identifying a biomarker may also include obtaining two SELDI spectra from a sample; subtracting the background from the spectra; truncating the spectra; scaling the peaks of the spectra; reducing the peaks of the spectra; determining if the two spectra should be combined; optionally combining the at least two spectra; and determining the distance dependent K-nearest neighbors.

Such methods may further comprise identifying significant peaks from the combined spectra or searching for outlier spectra.

The truncating is eliminating mass to charge ratios (m/z) values below 2500 Da, 2000 Da, 1500 Da, or below 1000 Da.

The scaling may be totaling the ion current to from between about 20000 to about 70000 for the sample.

The combining includes, for example, averaging the at least two spectra or keeping the spectra as duplicates.

The significant peaks are greater than 15% of the average intensity of a bin in the combined spectrum and not within 0.3% (M/Z) of a previously selected peak. Alternately, the significant peaks are greater than about 10-20% of the average intensity of a bin.

Diagnosis of Subject and Determination of Colorectal Cancer Status

Any biomarker, individually, is useful in aiding in the determination of colorectal cancer status. First, the selected biomarker is measured in a subject sample using the methods described herein, e.g., capture on a SELDI biochip followed by detection by mass spectrometry. Then, the measurement is compared with a diagnostic amount or control that distinguishes a colorectal cancer status from a non-colorectal cancer status. The diagnostic amount will reflect the information herein that a particular biomarker is up-regulated or down-regulated in a colorectal cancer status compared with a non-colorectal cancer status. As is well understood in the art, the particular diagnostic amount used can be adjusted to increase sensitivity or specificity of the diagnostic assay depending on the preference of the diagnostician. The test amount as compared with the diagnostic amount thus indicates colorectal cancer status.

While individual biomarkers are useful diagnostic markers, it has been found that a combination of biomarkers provides greater predictive value than single markers alone. Specifically, the detection of a plurality of markers in a sample increases the percentage of true positive and true negative diagnoses and would decrease the percentage of false positive or false negative diagnoses. Thus, preferred methods of the present invention comprise the measurement of more than one biomarker.

The detection of the marker or markers is then correlated with a probable diagnosis of colorectal cancer. In some embodiments, the detection of the mere presence or absence of a marker, without quantifying the amount of marker, is useful and can be correlated with a probable diagnosis of colorectal cancer. For example, biomarkers I-XIV can be more frequently detected in human colorectal cancer subjects than in normal subjects and/or in subjects who have non-colorectal cancer associated cytopenia. A mere detection of one or more of these markers in a subject being tested indicates that the subject has a higher probability of having colorectal cancer. In another embodiment, biomarkers I-XIV can be less frequently detected in human colorectal cancer subjects than in normal subjects, and/or in subjects who have non-colorectal cancer associated cytopenia. The mere detection of one or more of these markers in a subject being tested indicates that the subject has a lower probability of having colorectal cancer.

In other embodiments, the measurement of markers can involve quantifying the markers to correlate the detection of markers with a probable diagnosis of colorectal cancer. Thus, if the amount of the markers detected in a subject being tested is different compared to a control amount (i.e., higher or lower than the control, depending on the marker), then the subject being tested has a higher probability of having colorectal cancer.

The correlation may take into account the amount of the marker or markers in the sample compared to a control amount of the marker or markers (up or down regulation of the marker or markers) (e.g., in normal subjects or in non-colorectal cancer subjects such as where colorectal cancer is undetectable). A control can be, e.g., the average or median amount of marker present in comparable samples of normal subjects in normal subjects or in non-colorectal cancer subjects such as where colorectal cancer is undetectable. The control amount is measured under the same or substantially similar experimental conditions as in measuring the test amount. The correlation may take into account the presence or absence of the markers in a test sample and the frequency of detection of the same markers in a control. The correlation may take into account both of such factors to facilitate determination of colorectal cancer status.

In certain embodiments of the methods of qualifying colorectal cancer status, the methods further comprise managing subject treatment based on the status. As before the, management of the subject describes the actions of the physician or clinician subsequent to determining colorectal cancer status. For example, if the result of the methods of the present invention is inconclusive or there is reason that confirmation of status is necessary, the physician may order more tests (e.g., colonoscopy and imaging techniques). Alternatively, if the status indicates that treatment is appropriate, the physician may schedule the patient for treatment. In other instances, the patient may receive chemotherapy or radiation treatments, either in lieu of, or in addition to, surgery. Likewise, if the result is negative, e.g., the status indicates late stage colorectal cancer or if the status is otherwise acute, no further action may be warranted. Furthermore, if the results show that treatment has been successful, a maintenance therapy or no further management may be necessary. Managing may include, for example, in addition to further diagnostic tests, administering at least one therapeutic agent, administering radiation therapy, immunotherapy, hyperthermia, surgery, surgery followed or preceded by chemotherapy and/or radiation therapy, biotherapy, and taking no further action.

Therapeutic agents may include, one or more of hypomethylating agents, farnesyltransferase inhibitors, cytokines, immunomodulatory agents, hormones, and antibodies. For example, folic acid, fluorouracil, 5-FU irinotecan, oxaliplatin, leucovorin, 5-FU, irinotecan, levamisole, and low-dose leucovorin. Chemotherapy regimens may include, for example, AIO regimen (folic acid, fluorouracil (5-FU irinotecan), FOLFOX4 regimen (oxaliplatin, leucovorin, 5-FU), FOLFOX6 regimen (oxaliplatin, leucovorin, 5-FU), FOLFIRI regimen (folic acid, 5-FU, irinotecan), IFL (or Saltz) regimen (irinotecan, 5-FU, leucovorin), NCCTG regimen (5-FU, levamisole), or NCCTG regimen (5-FU, low-dose leucovorin).

The invention also provides for such methods where the biomarkers (or specific combination of biomarkers) are measured again after subject management. In these cases, the methods are used to monitor the status of the colorectal cancer, e.g., response to colorectal cancer treatment, remission of the disease or progression of the disease. Because of the ease of use of the methods and the lack of invasiveness of the methods, the methods can be repeated after each treatment the patient receives. This allows the physician to follow the effectiveness of the course of treatment. If the results show that the treatment is not effective, the course of treatment can be altered accordingly. This enables the physician to be flexible in the treatment options.

In another example, the methods for detecting markers can be used to assay for and to identify compounds that modulate expression of these markers in vivo or in vitro.

The methods of the present invention have other applications as well. For example, the markers can be used to screen for compounds that modulate the expression of the markers in vitro or in vivo, which compounds in turn may be useful in treating or preventing colorectal cancer in subjects. In another example, the markers can be used to monitor the response to treatments for colorectal cancer. In yet another example, the markers can be used in heredity studies to determine if the subject is at risk for developing colorectal cancer. For instance, certain markers may be genetically linked. This can be determined by, e.g., analyzing samples from a population of colorectal cancer subjects whose families have a history of colorectal cancer. The results can then be compared with data obtained from, e.g., colorectal cancer subjects whose families do not have a history of colorectal cancer. The markers that are genetically linked may be used as a tool to determine if a subject whose family has a history of colorectal cancer is pre-disposed to having colorectal cancer.

In a preferred embodiment of the invention, a diagnosis based on the presence or absence in a test subject of any the biomarkers of this invention is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

Methods of identifying a biomarker also include determining distant dependent K-nearest neighbors, as described infra.

Methods of the invention for determining the colorectal cancer status of a subject, include for example, obtaining a biomarker profile from a sample taken from the subject; and comparing the subject's biomarker profile to a reference biomarker profile obtained from a reference population, wherein the comparison is capable of classifying the subject as belonging to or not belonging to the reference population;

wherein the subject's biomarker profile and the reference biomarker profile comprise one or more markers listed in Table 1.

The method may further comprise repeating the method at least once, wherein the subject's biomarker profile is obtained from a separate sample taken each time the method is repeated.

Samples from the subject may be taken at any time, for example, the samples may be taken 24 hours apart or any other time determined useful.

Such comparisons of the biomarker profiles can determine colorectal cancer status in the subject with an accuracy of at least about 60%, 70%, 80%, 90%, 95%, and approaching 100% as shown in the examples which follow.

The reference biomarker profile can be obtained from a population comprising a single subject, at least two subjects, at least 20 subjects or more. The number of subjects will depend, in part, on the number of available subjects, and the power of the statistical analysis necessary to differentiate the peaks.

A method of treating colorectal cancer comprising administering to a subject suffering from or at risk of developing colorectal cancer a therapeutically effective amount of a compound capable of modulating the expression or activity of one or more of the biomarkers of Table 1.

A method of treating a condition in a subject comprising administering to a subject a therapeutically effective amount of a compound which modulates the expression or activity of one or more of the biomarkers of Table 1.

Compounds useful in methods disclosed herein include, enzyme inhibitors, cytotoxic drugs, cytokins, chemokines, antibodies, a DNA molecule, an RNA molecule, a small molecule, a peptide, and a peptidomimetic.

A method of qualifying colorectal cancer status in a subject comprising:

(a) measuring at least one biomarker in a sample from the subject, wherein the biomarker is selected from one or more of the biomarkers of Table 1, and (b) correlating the measurement with colorectal cancer status.

The method may also comprise the step of measuring the at least one biomarker after subject management.

Optionally, the methods of the invention may further comprise generating data on immobilized subject samples on a biochip, by subjecting the biochip to laser ionization and detecting intensity of signal for mass/charge ratio; and transforming the data into computer readable form; and executing an algorithm that classifies the data according to user input parameters, for detecting signals that represent biomarkers present in colorectal cancer subjects and are lacking in non-colorectal cancer subject controls.

Types of colorectal cancer that may be identified or differentiated from one another according to this method include adenocarcinoma, mucinous adenocarcinoma, signet-ring cell adenocarcinoma, squamous cell carcinoma, adenosquamous carcinoma, undifferentiated carcinoma, unclassified carcinoma, carcinoid tumors, or nonepithelial tumors.

Kits

In yet another aspect, the invention provides kits for qualifying colorectal cancer status and/or aiding a diagnosis of human colorectal cancer, wherein the kits can be used to detect the markers of the present invention. For example, the kits can be used to detect any one or more of the markers described herein, which markers are differentially present in samples of colorectal cancer subjects and normal subjects. The kits of the invention have many applications. For example, the kits can be used to differentiate if a subject has colorectal cancer or has a negative diagnosis, thus aiding a human colorectal cancer diagnosis. In another example, the kits can be used to identify compounds that modulate expression of one or more of the markers in in vitro or in vivo animal models for colorectal cancer.

In one embodiment, a kit comprises: (a) a substrate comprising an adsorbent thereon, wherein the adsorbent is suitable for binding a marker, and (b) instructions to detect the marker or markers by contacting a sample with the adsorbent and detecting the marker or markers retained by the adsorbent. In some embodiments, the kit may comprise an eluant (as an alternative or in combination with instructions) or instructions for making an eluant, wherein the combination of the adsorbent and the eluant allows detection of the markers using gas phase ion spectrometry.

Such kits can be prepared from the materials described above, and the previous discussion of these materials (e.g., probe substrates, adsorbents, washing solutions, etc.) is fully applicable to this section and will not be repeated.

In another embodiment, the kit may comprise a first substrate comprising an adsorbent thereon (e.g., a particle functionalized with an adsorbent) and a second substrate onto which the first substrate can be positioned to form a probe, which is removably insertable into a gas phase ion spectrometer. In other embodiments, the kit may comprise a single substrate, which is in the form of a removably insertable probe with adsorbents on the substrate. In yet another embodiment, the kit may further comprise a pre-fractionation spin column (e.g., Cibacron blue agarose column, anti-HSA agarose column, K-30 size exclusion column, Q-anion exchange spin column, single stranded DNA column, lectin column, etc.).

Optionally, the kit can further comprise instructions for suitable operational parameters in the form of a label or a separate insert. For example, the kit may have standard instructions informing a consumer how to wash the probe after a sample of blood serum is contacted on the probe. In another example, the kit may have instructions for pre-fractionating a sample to reduce complexity of proteins in the sample. In another example, the kit may have instructions for automating the fractionation or other processes.

In another embodiment, a kit comprises (a) an antibody that specifically binds to a marker; and (b) a detection reagent. Such kits can be prepared from the materials described above, and the previous discussion regarding the materials (e.g., antibodies, detection reagents, immobilized supports, etc.) is fully applicable to this section and will not be repeated. Optionally, the kit may further comprise pre-fractionation spin columns. In some embodiments, the kit may further comprise instructions for suitable operation parameters in the form of a label or a separate insert.

Optionally, the kit may further comprise a standard or control information so that the test sample can be compared with the control information standard to determine if the test amount of a marker detected in a sample is a diagnostic amount consistent with a diagnosis of colorectal cancer.

Use of Biomarkers for Colorectal Cancer in Screening Assays

The methods of the present invention have other applications as well. For example, the biomarkers can be used to screen for compounds that modulate the expression of the biomarkers in in vitro or in vivo, which compounds in turn may be useful in treating or preventing colorectal cancer in subjects. In another example, the biomarkers can be used to monitor the response to treatments for colorectal cancer. In yet another example, the biomarkers can be used in heredity studies to determine if the subject is at risk for developing colorectal cancer.

Thus, for example, the kits of this invention could include a solid substrate having a hydrophobic function, such as a protein biochip (e.g., a Ciphergen ProteinChip array) and a buffer for washing the substrate, as well as instructions providing a protocol to measure the biomarkers of this invention on the chip and to use these measurements to diagnose colorectal cancer.

Method for identifying a candidate compound for treating colorectal cancer may comprise, for example, contacting one or more of the biomarkers of Table 1 with a test compound; and determining whether the test compound interacts with the biomarker, wherein a compound that interacts with the biomarker is identified as a candidate compound for treating colorectal cancer.

Compounds suitable for therapeutic testing may be screened initially by identifying compounds which interact with one or more biomarkers listed in identified herein. By way of example, screening might include recombinantly expressing a biomarker of this invention, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of this invention, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers of this invention may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of this invention may also be measured. For example, the self-assembly of a multi-protein complex which includes one of the biomarkers of this invention may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of any of the biomarkers of this invention may be administered to subjects who are suffering from or are at risk of developing colorectal cancer or other cancer. For example, the administration of a test compound which increases the activity of a particular biomarker may decrease the risk of colorectal cancer in a patient if the activity of the particular biomarker in vivo prevents the accumulation of proteins for colorectal cancer. Conversely, the administration of a test compound which decreases the activity of a particular biomarker may decrease the risk of colorectal cancer in a patient if the increased activity of the biomarker is responsible, at least in part, for the onset of colorectal cancer.

At the clinical level, screening a test compound includes obtaining samples from test subjects before and after the subjects have been exposed to a test compound. The levels in the samples of one or more of the biomarkers of this invention may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers of this invention may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which-express, or are capable of expressing, one or more of the biomarkers of this invention may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with colorectal cancer, test compounds will be screened for their ability to slow or stop the progression of the disease.

Classification Algorithms

A dataset can be analyzed by multiple classification algorithms. Some classification algorithms provide discrete rules for classification; others provide probability estimates of a certain outcome (class). In the latter case, the decision (diagnosis) is made based on the class with the highest probability. For example, consider the three-class problem: healthy, benign, and cancer. Suppose that a classification algorithm (e.g. Nearest neighbor) is constructed and applied to sample A, and the probability of the sample being healthy is 0, benign is 33%, and cancer is 67%. Sample A would be diagnosed as being cancer. This approach, however, does not take into account any "fuzziness" in the diagnosis i.e. that there was a certain probability that the sample was benign. Therefore, the diagnosis would be the same as for sample B, which has a probability of 0 of being healthy or benign and a probability of 1 of being cancer.

EXAMPLES

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

It should be appreciated that the invention should not be construed to be limited to the examples which are now described; rather, the invention should be construed to include any and all applications provided herein and all equivalent variations within the skill of the ordinary artisan.

Example 1

A total of 147 serum samples were collected at the Department of Surgery, University Hospital Schleswig-Holstein, Campus Lübeck, Germany. As described below, these original 147 serum samples were then reduced to 139 after outlier detection. The training set consisted of 32 healthy controls and 52 subjects with colorectal malignancy (colorectal adenocarcinomas and metastases). The usefulness of the identified m/z values for prediction of malignant disease was tested with an independently collected, non-overlapping, blinded validation set of 55 samples. Serum samples were acquired under standardized conditions and in adherence with protocols approved by the local Institutional Ethical Review Board. Clinical data are summarized in Table 2.

TABLE 2

Clinical parameter of samples in the training set and the blinded validation set. Accuracy of class prediction of the validation set revealed 96.7% sensitivity, 100% specificity, 100% positive predictive value, and a negative predictive value of 94.4%.

| | | TRAINING Set | | VALIDATION Set | |
|---|---|---|---|---|---|
| | | Malignancy | Control | Malignancy | Control |
| Patients | | n = 52 * | n = 32 | n = 36 * | n = 19 * |
| Tumor (T), | | (T = 33, | | (T = 17, | |
| Metastasis (M) | | M = 19) | | M = 19) | |
| SELDI Spectra | | n = 60 | n = 34 | n = 44 | n = 23 |
| Tumor (T), | | (T = 39, | | (T = 22, | |
| Metastasis (M) | | M = 21) | | M = 22) | |
| Sex | Female | 23 | 16 | 11 | 12 |
| | Male | 29 | 16 | 25 | 7 |
| Age | (average in years) | 62.9 | 31.3 | 64.9 | 36.8 |
| | (range in years) | (39-81) | (19-43) | (42-81) | (26-61) |
| UICC | UICC I | 6 | | 5 | |
| Staging | UICC II | 10 | | 4 | |
| | UICC III | 16 | | 3 | |
| | UICC IV | 20 | | 24 | |
| TNM | T1 | 2 | | 2 | |
| Staging | T2 | 6 | | 4 | |
| | T3 | 20 | | 10 | |
| | T4 | 5 | | 1 | |
| Local- | Caecum | 1 | | 1 | |
| ization | Ascendens | 0 | | 2 | |
| | Transversum | 1 | | 0 | |
| | Descendens | 0 | | 1 | |
| | Sigmoideum | 10 | | 5 | |
| | Rectum | 21 | | 8 | |
| Metas- | Liver | 7 | | 16 | |
| tasis | Lung | 5 | | 1 | |
| | Liver&Lung | 3 | | 2 | |
| | Recurrency | 4 | | 0 | |

| | | Malignancy n = 36 | Control n = 19 |
|---|---|---|---|
| Classification into | | | |
| Malignancy | (Sensitivity: 96.7%) | 30 | 0 |
| Control | (Specificity: 100%) | 1 | 17 |
| Not classifiable | (12.7%) | 5 | 2 |

* Samples identified as outliers were excluded from the analysis. Those samples, not represented in the above table, showed the following clinical characteristics: TRAINING SET - MALIGNANCIES: Six outliers (56-year-old female patient with rectal carcinoma, UICC III/57-year-old male patient with colon sigmoideum carcinoma, UICC III/54-year-old female patient with rectal carcinoma, UICC I/78-year-old male patient with colon sigmoideum carcinoma, UICC I/77-year-old female patient with rectal carcinoma, UICC II/60-year-old male patient with liver metastasis, UICC IV). TRAINING SET - CONTROL: No outliers. VALIDATION SET - MALIGNANCIES: One outlier (71-year-old male patient with rectosigmoid carcinoma and liver metastasis, UICC IV). VALIDATION SET - CONTROL: One ooltier (46-year-old male patient without any signs of malignancy).

Method of Examination

The Ciphergen chip data were treated as described in FIG. 1: Background subtraction using Ciphergen software was followed by truncation of the spectra to eliminate m/z values below 1500 Da. Values below that range can be due to noise inherent to SELDI-TOF based protein profiling. After scaling each spectrum to a constant total ion current, the spectra were combined to identify peak regions with sufficient intensity: 648 peaks were identified on the IMAC3 platform, and 761 peaks on the WCX2 chip. The spectra of the two chip surfaces were then combined, such that each spectrum presented 1445 features. It was then determined if the duplicate spectra (two technical repeats per serum sample) should be averaged or kept as duplicates. Outlier detection identified eight samples that were excluded from subsequent analysis. Only training set spectra were then used to identify features that distinguish malignant sample sera from control sera: through model building based on evolutionary programming, a total of 16 top models selected a set of 13 features that were chosen in different combinations by Distance-Dependent K-Nearest Neighbors (DD-KNN) (Table 3).

TABLE 3

Features found in the 16 DD K-Nearest Neighbors models using the combined IMAC-WCX dataset.

| Peak (m/z) | 2 Features | 3 Features | 4 Features | 5 Features |
|---|---|---|---|---|
| 2591.1i | | 8, 9 N | | |
| 5715.9i | 9 N | | | |
| 7005.2i | | | | 6, 7, 8, 9 N |
| 7568.9i | | 7 N | 9 N | |
| 7683.6i | | 6 N | | |
| 7722.6i | | | | 9 N |
| 7905.8i | | | 6, 7, 8 N | 6, 7, 8 N |
| 9148.7i | 6, 7, 8, 9 N | 6, 7, 8, 9 N | 6, 7, 8, 9 N | 6, 7, 8, 9 N |
| 14653.8i | | 6, 7, 8, 9 N | | 6, 7, 8 N |
| 14698.6i | | | | 9 N |
| 2172.8w | | | 6, 7, 8 N | |
| 2646.9w | | | 6, 7, 8, 9 N | 6, 7, 8, 9 N |
| 9556.6w | 6, 7, 8 N | | | |

Abbreviations: i, feature on IMAC chip; w, feature on WCX chip; N, neighbors.

The value of these features for the detection of colorectal malignancy was then tested with an independently collected, blinded validation set consisting of 55 samples. For this purpose, Maximum Likelihood was used for class prediction in all 16 models that were based on K-Nearest-Neighbors. Only samples that revealed identical results with all 16 models were considered for further classification into the malignant or healthy group (Table 4). All analytical procedures were completed before patient diagnoses were decoded.

A comprehensive evaluation of serum protein patterns from 88 subjects with colorectal malignancy and 51 healthy individuals was made using SELDI-TOF mass spectrometry. The first step of the analytical procedure focused on the characterization of 32 healthy controls and 52 samples with colorectal malignancy. This training set was used to identify differentially expressed m/z values, or features, between the two groups. These features were then used to classify an independently collected series of serum samples (n=55). This validation set was analyzed in double-blinded fashion.

Figure 2:
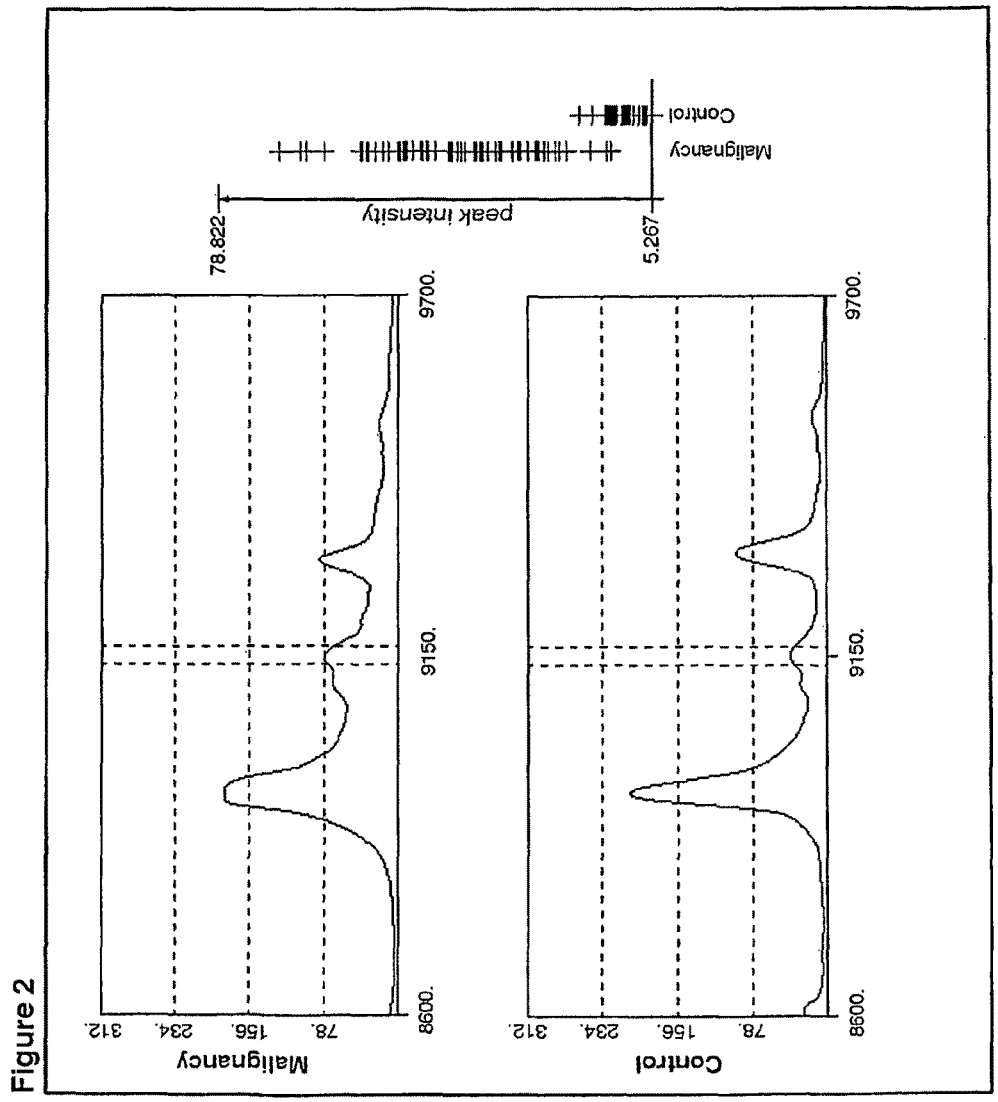
FIG. 2 shows spectrum and ratio plots for the feature 9148.7 m/z used in all 16 DD K-Nearest Neighbors models. The spectrum at the top represents a sample of the malignancy group and the one at the bottom represents a control sample. The plot on the right side indicates the peak intensities for 9148.7 m/z denoted by a cross for each malignancy spectra (left side) and each control spectra (right side) of the training set. Note the profound differences in expression levels.
Figure 4:
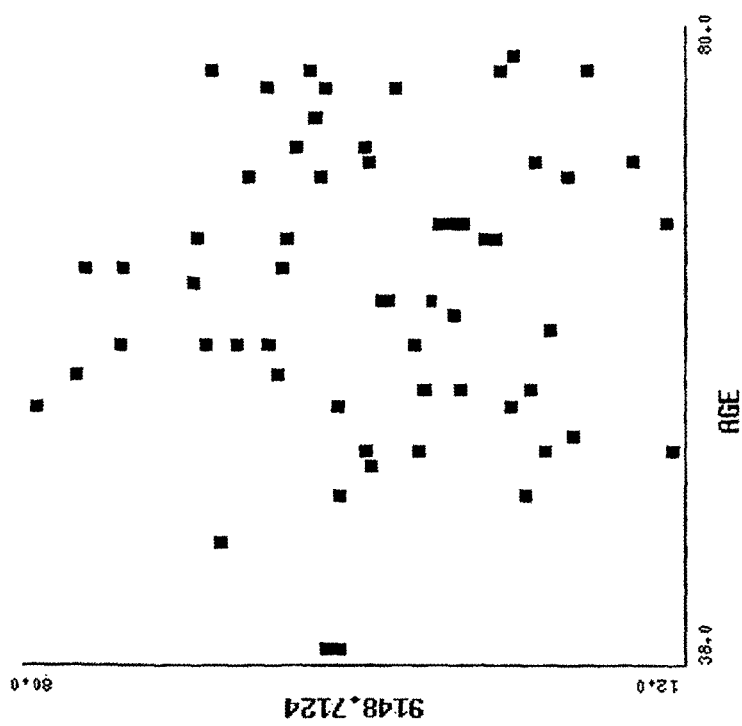
FIG. 4 depicts Scatter plot of peak intensity versus age (years) for all malignancy samples included in the training set. Note that there is no correlation (Pearson's r=−0.04221) between age and peak intensity for the dominant feature at 9148.7 m/z. Molecular weights and m/z values are listed in Daltons.

The comparison of 52 subjects with colorectal malignancy with 32 healthy controls revealed a set of 13 features that were chosen in different combinations by K-Nearest Neighbors to distinguish the malignant sera from healthy control sera. The 13 discriminative features were located at the following m/z values: 2172.8, 2591.1, 2646.9, 5715.9, 7005.2, 7568.9, 7683.6, 7722.6, 7905.8, 9148.7, 9556.6, 14653.8, and 14698.6 Da One of the m/z values, at 9148.7 Da, was selected by all 16 models and therefore appears to be the strongest single discriminative feature. FIG. 2 exemplifies the peak intensities of all training set samples and spectra from a malignant and a control sample for this dominant feature. Since the control sera were collected from significantly younger individuals as compared to the malignant sera (Table 1), each selected feature was analyzed for the possibility that the observed differences might simply be a reflection of age. No age-dependent expression of certain features was detected; for instance, the most dominant feature at 9148.7 m/z revealed a Pearson's correlation coefficient of expression levels and age of $r=-0.04221$, indicating that there is no correlation between expression levels and age (FIG. 4). The analysis of the training set therefore suggested that serum profiling using SELDI-TOF identifies protein peaks that allow the discernment of subjects with colorectal malignancy from control individuals. The predictive value of these 13 features was then tested with an independently collected, blinded validation set consisting of 55 samples. For this purpose 16 models were used based on DD-K-Nearest-Neighbors comprising two, three, four or five selected features and six to nine neighbors. Only samples that revealed identical results with all 16 models were considered for further classification into the malignant or control group (Table 4). Applying this criterion, 48 of 55 samples were classifiable.

TABLE 4

A total of 16 DD K-Nearest Neighbors models, using 2 to 5 features and 6 to 9 neighbors, were utilized for class prediction of the validation set samples. Note that all 16 models had to agree with each other in order to allow class prediction. If all 16 models did not agree, the sample was declared as not classifiable (n.c.) and not used for class prediction (e.g., sample 5).

| Sample Type | Sample | Spectra | IMAC3-WCX Sample | | | | 2 Features | | | | 3 Features | | | | 4 Features | | | | 5 Features | | | | Result | Correct predicted |
|---|---|---|---|---|---|---|---|---|---|---|---|---|---|---|---|---|---|---|---|---|---|---|---|---|
| | | | 6N | 7N | 8N | 9N | 6N | 7N | 8N | 9N | 6N | 7N | 8N | 9N | 6N | 7N | 8N | 9N | 6N | 7N | 8N | 9N | | |
| M | 1 | 1 | M | M | M | M | M | M | M | M | M | M | M | M | M | M | M | M | M | Yes |
| M | 2 | 2 | M | M | M | M | M | M | M | M | M | M | M | M | M | M | M | M | M | Yes |
| C | 3 | 3 | C | C | C | C | C | C | C | C | C | C | C | C | C | C | C | C | C | Yes |
| M | 4 | 4 | M | M | M | M | M | M | M | M | M | M | M | M | M | M | M | M | M | Yes |
| C | 5 | 5 | C | C | C | C | C | M | C | C | M | M | C | C | C | C | C | C | n.c. | |
| M | 6 | 6 | M | M | M | M | M | M | M | M | M | M | M | M | M | M | M | M | M | Yes |
| M | 7 | 7 | M | M | M | M | M | M | M | M | M | M | M | M | M | M | M | M | M | Yes |
| M | 8 | 8 | M | M | M | M | M | M | M | M | M | M | M | M | M | M | M | M | M | Yes |
| C | 9 | 9 | C | C | C | C | C | C | C | C | C | C | C | C | C | C | C | C | C | Yes |
| M | 10 | 10 | M | M | M | M | M | M | M | M | M | M | M | M | M | M | M | M | M | Yes |
| C | 11 | 12 | C | C | C | C | C | C | C | C | C | C | C | C | C | C | C | C | C | Yes |
| M | 12 | 13 | C | C | C | M | M | M | M | M | C | C | C | C | C | C | C | C | n.c. | |
| M | 13 | 14 | M | M | M | M | M | M | M | M | M | M | M | M | M | M | M | M | M | Yes |
| M | 14 | 15 | C | C | C | C | M | C | C | C | C | C | C | C | C | C | C | C | n.c. | |
| C | 15 | 16, 17 | C, C | C, C | C, C | C, C | C, C | C, C | C, C | C, C | C, C | C, C | C, C | C, C | C, C | C, C | C, C | C, C | C | Yes |
| M | 16 | 18 | M | M | M | M | M | M | M | M | M | M | M | M | M | M | M | M | M | Yes |
| M | 17 | 19 | M | M | M | M | M | M | M | M | M | M | M | M | M | M | M | M | M | Yes |
| M | 18 | 20 | M | M | M | M | M | M | M | M | M | M | M | M | M | M | M | M | M | Yes |
| C | 19 | 21, 22 | C, C | C, C | C, C | C, C | C, C | C, C | C, C | C, C | C, C | C, C | C, C | C, C | C, C | C, C | C, C | C, C | C | Yes |
| C | 20 | 25 | C | C | C | C | C | C | C | C | C | C | C | C | C | C | C | C | C | Yes |
| M | 21 | 26 | M | M | M | M | M | M | M | M | M | M | M | M | M | M | M | M | M | Yes |
| C | 22 | 27 | C | C | C | C | C | C | C | C | C | C | C | C | C | C | C | C | C | Yes |
| M | 23 | 28 | M | M | M | M | M | M | M | M | M | M | M | M | M | M | M | M | M | Yes |
| M | 24 | 29 | M | M | M | M | M | M | M | M | M | M | M | M | M | M | M | M | M | Yes |
| M | 25 | 30 | M | M | M | M | M | M | M | M | M | M | M | M | M | M | M | M | M | Yes |
| C | 26 | 31 | C | C | C | C | C | C | C | C | C | C | C | C | C | C | C | C | C | Yes |
| C | 27 | 32 | C | C | C | C | C | C | C | C | C | C | C | C | C | C | C | C | C | Yes |
| M | 28 | 33, 34 | M, M | M, M | M, M | M, M | M, M | M, M | M, M | M, M | M, M | M, M | M, M | M, M | M, M | M, M | M, M | M, M | M | Yes |
| M | 29 | 35, 36 | M, M | M, M | M, M | M, M | M, M | M, M | M, M | M, M | M, M | M, M | M, M | M, M | M, M | M, M | M, M | M, M | M | Yes |
| C | 30 | 37 | C | C | C | C | C | C | C | C | C | C | C | C | C | C | C | C | C | Yes |
| C | 31 | 38, 39 | C, C | C, C | C, C | C, C | C, C | C, C | C, C | C, C | C, C | C, C | C, C | C, C | C, C | C, C | C, C | C, C | C | Yes |
| M | 32 | 40 | M | M | M | M | M | M | M | M | M | M | M | M | M | M | M | M | M | Yes |
| M | 33 | 41 | M | M | M | M | M | M | M | M | M | M | M | M | M | M | M | M | M | Yes |
| M | 34 | 42 | M | M | M | M | M | M | M | M | M | M | M | M | M | M | M | M | M | Yes |
| M | 35 | 43, 44 | C, C | C, C | C, C | C, C | M, ? | M, C | M, C | M, C | M, C | M, C | M, C | M, C | M, C | M, C | M, C | M, C | n.c. | |
| C | 36 | 45 | C | C | C | C | C | C | C | C | C | C | C | C | C | C | C | C | C | Yes |
| C | 37 | 46 | C | C | C | M | C | C | C | C | M | M | C | M | M | M | C | C | n.c. | |
| M | 38 | 47, 48 | M, C | M, C | M, C | M, C | M, M | M, C | M, C | M, C | M, C | M, C | M, C | M, C | M, C | M, C | M, C | M, C | n.c. | |
| M | 39 | 49, 50 | C, C | C, C | C, C | C, C | C, C | C, C | C, C | C, C | C, C | C, C | C, C | C, C | C, C | C, C | C, C | C, C | C | NO |
| C | 40 | 51 | C | C | C | C | C | C | C | C | C | C | C | C | C | C | C | C | C | Yes |
| M | 41 | 52 | M | M | M | M | M | M | M | M | M | M | M | M | M | M | M | M | M | Yes |
| C | 42 | 53, 54 | C, C | C, C | C, C | C, C | C, C | C, C | C, C | C, C | C, C | C, C | C, C | C, C | C, C | C, C | C, C | C, C | C | Yes |
| M | 43 | 55, 56 | M, M | M, M | M, M | M, M | M, M | M, M | M, M | M, M | M, M | M, M | M, M | M, M | M, M | M, M | M, M | M, M | M | Yes |

TABLE 4-continued

A total of 16 DD K-Nearest Neighbors models, using 2 to 5 features and 6 to 9 neighbors, were utilized for class prediction of the validation set samples. Note that all 16 models had to agree with each other in order to allow class prediction. If all 16 models did not agree, the sample was declared as not classifiable (n.c.) and not used for class prediction (e.g., sample 5).

| Sample Type | Sample | IMAC3-WCX Spectra | 2 Features 6N | 7N | 8N | 9N | 3 Features 6N | 7N | 8N | 9N | 4 Features 6N | 7N | 8N | 9N | 5 Features 6N | 7N | 8N | 9N | Result | Correct predicted |
|---|---|---|---|---|---|---|---|---|---|---|---|---|---|---|---|---|---|---|---|---|
| M | 44 | 57 | M | M | M | M | M | M | M | M | M | M | M | M | M | M | M | M | M | Yes |
| M | 45 | 58 | M | M | M | M | M | M | M | M | M | M | M | M | M | M | M | M | M | Yes |
| M | 46 | 59, 60 | M, M | M, M | M, M | M, M | M, M | M, M | M, M | M, M | M, M | M, M | M, M | M, M | M, M | M, M | M, M | M, M | M | Yes |
| M | 47 | 61 | M | M | M | M | M | M | M | M | M | M | M | M | M | M | M | M | M | Yes |
| M | 48 | 62, 63 | C, M | M, M | M, M | M, M | M, M | M, M | M, M | M, M | M, M | M, M | M, M | M, M | M, M | M, M | M, M | M, M | n.c. | |
| C | 49 | 64 | C | C | C | C | C | C | C | C | C | C | C | C | C | C | C | C | C | Yes |
| C | 50 | 65 | C | C | C | C | C | C | C | C | C | C | C | C | C | C | C | C | C | Yes |
| M | 51 | 66 | M | M | M | M | M | M | M | M | M | M | M | M | M | M | M | M | M | Yes |
| M | 52 | 67 | M | M | M | M | M | M | M | M | M | M | M | M | M | M | M | M | M | Yes |
| M | 53 | 68 | M | M | M | M | M | M | M | M | M | M | M | M | M | M | M | M | M | Yes |
| C | 54 | 69 | C | C | C | C | C | C | C | C | C | C | C | C | C | C | C | C | C | Yes |
| M | 55 | 70 | M | M | M | M | M | M | M | M | M | M | M | M | M | M | M | M | M | Yes |
| Number of samples out of 55 samples that could be classified based upon the agreement of 16 models | | | | | | | | | | | | | | | | | | | 48 | 98% |
| Percentage of samples out of 55 samples that could be classified based on the agreement of 16 models | | | | | | | | | | | | | | | | | | | 87% | |

Abbreviations; 6N, 6 neighbors; 7N, 7 neighbors; 8N, 8 neighbors; 9N, 9 neighbors; C, control; M, malignancy; ?, 50% predictive value for M and C; n.c., not classifiable.

Of those 48 samples, 47 were classified correctly (98%). The sera from the seven individuals that revealed ambiguous class predictions—i.e., not all 16 classifiers agreed with one another—belonged to two healthy controls (a 30-year-old female and a 35-year-old male) and five tumor subjects with carcinomas classified as T3N0MX, T3N1MX (twice), 72N0MX, and T1N0MX. One of these subjects had a synchronous gastrointestinal stromal tumor. Three of the five tumors were localized at the right colon, a location that was underrepresented in the training set (Table 2). Four of the five not classifiable tumors had been operated with curative attempt (R0 resection), whereas one tumor could be resected only incompletely (R2 resection). The latter tumor is one of three inoperable tumors that were included in the validation set Only one advanced, inoperable tumor, however, was included in the training set and hence its characteristics were underrepresented for classifier training. This might also explain that the only misclassified sample represented an inoperable tumor (a 63-year-old male patient with an advanced staged rectal carcinoma with synchronous metastasis (UICC IV)). The technical repeats for this sample were analyzed separately and were assigned to the healthy control group with very high probability (55% to 97% likelihood). This rather surprising lack of sensitivity for the detection of advanced tumors could be due not only to the under-representation of such advanced malignancies in the training set but potentially also due to the following factors: (A) Highly advanced tumors with early metastasis potential might have a different protein profile than primary tumors and/or their metastasis alone. Certain proteins might be expressed exclusively in these advanced tumors and—compared to features that are normally expressed from less advanced cancers—could reach higher peak intensities. Due to normalization, the dominant features used for classification would be scaled down and thus the advanced tumor would not be classifiable or even determined to be normal. (B) Another possible explanation is that dominant features used for classification might be expressed only temporarily and become less prominent or disappear during progression towards advanced tumor stages. A repeated SELDI-TOF analysis of the misclassified sample together with an additional serum sample from the same patient showed that the spectra of this particular patient were then defined as outliers; this might confirm the above discussed hypotheses. The classifiers applied were designed more for the identification of potential biomarkers, rather than for the creation of the best possible classifier. This is different from several previous studies that employed SELDI-TOF mass spectrometry for detection of, e.g., ovarian carcinomas (10). In these studies, an overall scaling of each spectrum was performed once instead of scaling each feature over the set of samples or scaling over a selected set of features. In addition, our classifiers were only allowed to use a small number of features (2 to 5) and a relatively large number of neighbors (6 to 9); these stringent conditions render it very difficult to produce a fortuitous separation of samples into regions containing members of the same class.

The observation that two control and five malignant sera were not classifiable does not impair the usefulness of SELDI based KNN-classification as a powerful screening tool. Individuals whose sera cannot be classified with certainty would have to undergo conservative medical examination. None of the normal samples was assigned to the malignant group. The SELDI based KNN-classification presented here, identified 13 features that permitted the discrimination of colorectal cancer-associated sera from healthy controls in an independent, blinded validation with 96.7% sensitivity, 100% specificity, 100% positive predictive value, and 94.4% negative predictive value (Table 2). In comparison, Cordero et al. determined a sensitivity and specificity of 90% for colorectal cancer diagnosis by using preoperative serum CD26 levels (11). Any other diagnostic approach, such as detection of CEA or VEGF, TIMP1, circulating D-diner, IL-6, or CRP concentrations either alone or in combination reaches only lower diagnostic efficiencies (12-18). Real time quantification of human telomerase reverse transcriptase mRNA in plasma obtained a sensitivity of 98%, but a specificity of only 64% (19). None of these markers showed high enough discriminative power to become implemented in clinical tumor screening. One similar approach to detect colorectal malignancy by SELDI-TOF based protein profiling was performed by Yu et al. (20). Their results suggest that colorectal cancer subjects can be discriminated from healthy controls with 89% sensitivity and 92% specificity based on four features. These four features showed different m/z values than the 13 features identified in our analysis. Yu and colleagues did not verify their findings with an independent validation set.

Figure 3:
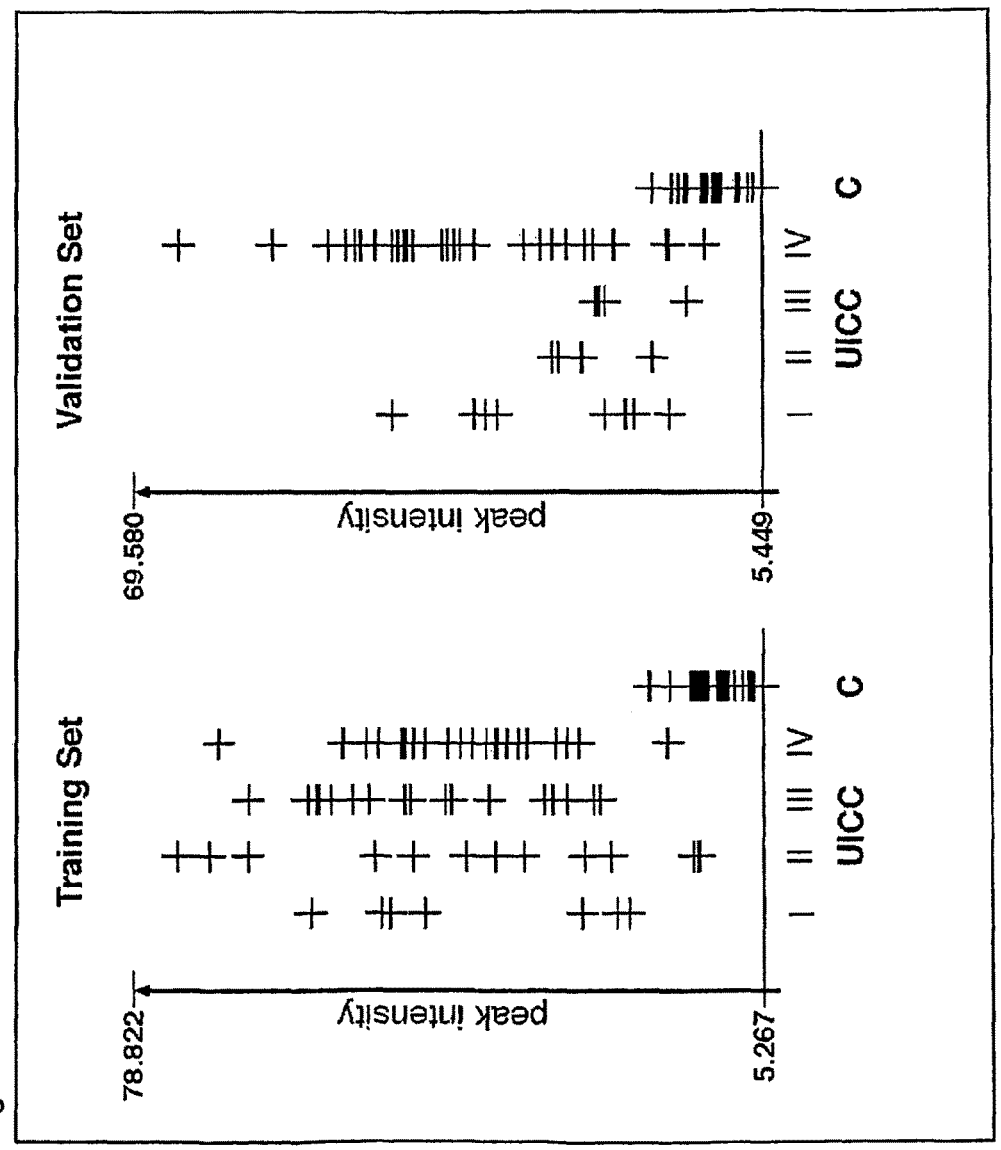
FIG. 3 depicts a ratio plot of peak intensities for the feature 9148.7 m/z used in all 16 DD K-Nearest Neighbors models for the training (left) and validation (right) set. The peak intensities (one cross per spectrum/sample) are grouped according to the UICC stage of the malignancies (first four columns to the left, respectively) and are compared to peak intensities of the control (C) spectra (right column). Note that there is no correlation between peak intensity and the UICC stage in neither the training nor the validation set.

Early detection of cancer is a perceived clinical goal. A total of 16 tumor samples in the training set tested here, were UICC stage I and II, i.e., early stage tumors. The independent validation set contained nine such tumors. FIG. 3 shows the plot of the peak intensities according to the UICC stage of the malignant sera compared to the control sera for the strongest discriminative feature at 9148.7 m/z. The figure demonstrates that there is no correlation between peak intensity and tumor stage. Thus, our SELDI based protein profiling with KNN class prediction based on 13 features presents a highly sensitive and specific diagnostic approach that distinguishes sera from colorectal cancer subjects, including those with early stage disease, from healthy controls. These results now warrant further analyses that employ even larger sample sets collected from different clinics.

Sample Preparation

Serum samples were acquired under standardized conditions and in adherence with protocols approved by the local Institutional Ethical Review Board. Samples were stored at −80° C. until processed for SELDI analysis. Samples were processed according to protocols provided by the manufacturer of the two protein chips utilized (IMAC3: immobilized metal affinity capture array with a nitriloacetic acid surface; WCX2: weak cation exchange array with carboxylate functionality).

Serum samples were thawed on ice and subsequently diluted 1:1 in 9M Urea/2% CHAPS. Following 30 minutes incubation on ice, samples for IMAC3 chip use were diluted 1:5 in PBS, pH 7.4+0.1% Triton X-100, whereas samples for WCX2 application were diluted 1:5 in 50 mM sodium acetate, pH 4.5+0.1% Triton X-100. All samples were stored on ice until ready to use. After bioprocessor set up, both chip platforms were pretreated: all solutions were incubated at room temperature with gentle agitation and decanted before new solution was applied. The IMAC3 chip was incubated with 100 µl/well of 100 mM $CuSO_4$ for 10 minutes with one repeat followed by a brief wash with 200 µl/well of HPLC-grade water for 30 seconds. Then, 100 µl/well of 50 mM sodium acetate pH 4.0 were incubated for 10 minutes before 200 µl/well of HPLC-grade water were applied for 30 seconds. The WCX2 chip was incubated with 100 µl/well of 10 mM HCl for 10 minutes followed by application of 200 µl/well of HPLC-grade water for 5 minutes. After pretreatment of the chip surfaces each well of the bioprocessor was incubated with 100 µl of binding/wash buffer according to the chip to be used (IMAC3: PBS, pH 7.4+0.1% Triton X-100; WCX2: 50 mM sodium acetate, pH 4.5+0.1% Triton X-100). After 15 minutes incubation, 100 µl sample were added to each well of the bioprocessor. The bioprocessor was covered and incubated for 1.5 hours at room temperature while shaking. Samples were then removed and each well of the bioprocessor was washed three times with 100 µl of the binding/wash buffer as specified above for 5 minutes each. Additionally, 200 µl of final wash buffer were added to each well of the bioprocessor and incubated for 30 seconds with shaking (IMAC3: 5 mM Tris, pH 8.0; WCX2: HPLC grade water). Incubation with final wash buffer was repeated once. Protein chips were removed from the bioprocessor and air-dried.

Both protein chips were analyzed on the Protein Biology System 2 SELDI-TOF mass spectrometer (Ciphergen Biosystems, Freemont, Calif., USA). Mass accuracy is assessed daily through external calibration utilizing a standard mixture obtained from Ciphergen (dynorphin A (2147.5), ACTH 1-24 (2933.5), Beta-Endorphin (3465.0), bovine insulin (5733.6), ubiquitin (8564.8), bovine cytochrome C (12230.9), and bovine beta lactoglobulin A (18363.3)). One µL of a saturated sinapinic acid solution in 50% acetonitrile, 0.5% trifluoroacetic acid was added to each spot of the proteinchip array. The arrays were then analyzed using the following PBS-II SELDI-TOF MS automated settings: IMAC3: laser intensity 215, detector sensitivity 8, focus mass 5000, m/z range 0-200,000, 130 averaged laser shots per sample spectrum. WCX2: laser intensity 220, detector sensitivity 8, focus mass 5000, m/z range 0-200,000, 130 averaged laser shots per sample spectrum. Data were collected using Ciphergen ProteinChip software version 3.0.2.

Method of Examination

A total of 147 serum samples were collected at the Department of Surgery, University Hospital Schleswig-Holstein, Campus Lübeck, Germany. As described below, these original 147 serum samples were then reduced to 139 due to outlier detection. The sample numbers presented in the publication exclusively refer to the reduced number of 139 serum samples, whereas the analysis as described below refers to the total number of 147 serum samples.

The baseline-subtracted spectra from the IMAC3 and WCX2 chip surfaces contained 116 cancer spectra (duplicate spectra from 58 subjects with colon malignancy), 64 control spectra (duplicate spectra from 32 individuals with no signs of colon cancer), and 114 blinded samples (duplicate spectra from 57 individuals). They were independently collected from M/Z=14999.96 to 96000.39 Da (29306 bins), and scaled to a total ion current of 50000.0 for each sample. The 180 spectra of the training set from a given chip surface were then summed together at each M/Z value and this summed spectrum was used to find significant peaks. In this study, a peak was deemed significant if its intensity was greater than 15% of the average intensity of a bin in the summed spectrum and was not within 0.3% (M/Z) of a previously selected peak. This was accomplished by finding the bin with the highest intensity in the summed spectrum and by placing that M/Z value in a peak list. The intensity of this bin and all other bins within 0.3% (M/Z) were set to zero. The process continued by finding the highest intensity peak in the remaining summed spectrum, adding it to the peak list and zeroing out that region of the summed spectrum until the highest remaining peak had an intensity below the threshold. The next step was to return to each individual spectrum and reduce it to those peaks in the appropriate peak list. This was done by placing a read-window of width 0.3% (M/Z) centered at each M/Z value in the peak list and storing the maximum intensity found in any bin within the read-window. For the IMAC3 spectra, a total of 684 significant peaks were obtained, while for the WCX2 surface, 761 significant peaks were identified.

These scaled, reduced spectra from each chip surface were then combined for each sample, resulting in a dataset that contained 1445 significant peaks for 180 samples in the training set and 114 samples in the validation set. These combined spectra were then examined to determine if the duplicate spectra should be averaged or kept separate. If the duplicate spectra for a given subject were sufficiently different from each other, then either one or both may either represent a valid spectrum for a subject in their particular class (cancer or healthy) or may be an erroneous spectrum caused by some unknown problem in sample collection or spectral production. In either case, the spectra should be kept as separate results. Conversely, if the duplicate spectra are sufficiently similar, keeping them separate may artificially bias the classification towards good results. In this case the spectra should be averaged. To determine if a given duplicate pair should be averaged, the Euclidean distance over all scaled, reduced peaks were determined for all spectra within a given class. The number of spectra that were closer to each member of the duplicate pair than this pair was to each other was recorded, and if this total exceeded four the spectra were kept separate. Otherwise, the spectra were averaged. Of the 58 duplicate spectra from subjects with colon cancer, 48 were averaged and the remaining 10 duplicates were kept separate. For the spectra from healthy subjects, 30 of the 32 duplicate pairs were averaged and the remaining two pairs were kept separate. For the blinded set, 45 of the 57 duplicate spectra were averaged and the remaining 12 pairs were kept separate.

At this point the training set contained 102 spectra (68 cancer and 34 healthy) and the testing set contained 69 spectra. The next step was to search for outlier spectra. First, the training and testing spectra were combined, and the Euclidean distance to the nearest neighbor over the 1445 peak intensities was determined. These 174 nearest-neighbor distances were used to calculate an average nearest-neighbor distance and a standard deviation. If a spectrum had a nearest-neighbor distance that was more than two standard deviations above the mean, it was labeled as a Type-1 outlier. In the second examination, the minimum and maximum intensity for each peak was recorded. For each spectrum, the intensities were examined and the number of times a peak's intensity was in the lower or upper 5% of the range was counted. These 174 counts were used to determine an average number of 5%-extrema and a standard deviation. If a spectrum's number of 5%-extrema was more than two standard deviations above the average, it was denoted a Type-2 outlier. All spectra that were either Type-1 or Type-2 outliers were removed from the dataset. This reduced the number of cancer spectra to 60 and the number of blinded spectra to 67, while none of the 34 healthy spectra was found to be outliers.

The 60 cancer spectra and 34 healthy spectra were used to construct 16 different classifiers. A set of J features was used to build a classifier based on a Distance-Dependent K-Nearest Neighbors algorithm. These J features placed each sample in the training set on a point in J-dimensional space. For the $i^{th}$ training sample, the K other training samples with the smallest Euclidean distance were placed in this sample's neighbor list. The un-normalized probability that the $i^{th}$ training sample is in the same class as its $k^{th}$ neighbor (Ck) is given by the following expression.

$$p(Ck)=\alpha/Dik$$

Dik is the Euclidean distance to this neighbor and $\alpha$ is set so that the probability is reduced to 0.5 if Dik is 10% of the maximum distance between training samples in this J-dimensional space. This reduces the probability that it is in the same class as its neighbor as the distance to this neighbor increases. This does not account for the situation when a given sample is far away from all of its neighbors in this J-dimensional space, and so the un-normalized probability that this sample is undetermined relative to the $k^{th}$ neighbor is also determined. This probability, p(Uk), is set to a constant Cu (Cu=0.1 in this study) if p(Ck) is less than (1-2Cu), decreases as (1-p(Ck)/2) as p(Ck) increases from (1-2Cu) to 1.0, and is zero if p(Ck) is greater than 1.0. If the $k^{th}$ neighbor is cancerous, then the un-normalized probability that this $i^{th}$ sample is cancerous, $p_i(C)$, is increased by p(Ck), otherwise the un-normalized probability that it is normal, $p_i(N)$, is increased by this amount. In addition, the un-normalized probability that it is undetermined, $p_i(U)$, is increased by p(Uk) independent of the class of this neighbor. Once this is done for all neighbors, the normalized probability that the $i^{th}$ training sample is correctly classified is given by the following expression if this training sample is cancerous.

$$P_i(\text{Correct})=p_i(C)/[p_i(C)+p_i(N)+p_i(U)]$$

If the $i^{th}$ training sample is normal, the following probability is used instead.

$$P_i(\text{Correct})=p_i(N)/[p_i(C)+p_i(N)+p_i(U)]$$

The overall cost of this set of J features is the sum of $(1-P_i(\text{Correct}))$ over all training samples. The goal is then to find the set of J features that minimizes the overall cost for a given value of K (number of neighbors).

The 16 classifiers constructed in this study use two, three, four or five features (J=2, 3, 4, 5) and six, seven, eight or nine neighbors (K=6, 7, 8, 9). Given that the training set contains 1445 peak intensities (features) for each sample, there are over $5.2 \times 10^{13}$ unique sets of five features. Examining all possible combinations for a given value of K is not practical, so a modified Evolutionary Programming algorithm is used to search for the optimum set of J features. The algorithm, as employed here, starts with a population of Np sets of J features, ensuring that each set is unique. The overall cost of each of these sets is determined and stored. Each member of this population creates a new set of J features (an offspring) by randomly selecting one or two of the features in the parent's set and replacing them with unused features selected at random. The remaining features are the same as those in the parent's set. The modification employed here checks the offspring's set of J features to ensure that it is different from any member of the parent population and any offspring generated so far. If it is found to be the same, it is discarded and the parent generates a new offspring. The overall cost of this offspring's set of J features is determined and this set of features and its cost is stored in an offspring population. Once all parents have generated an offspring, the two populations are combined and the Np sets of J features with the lowest overall cost are retained. This completes a generation and the Np sets of J features with the lowest cost become parents for the next generation. This continues for Ng generations. For the results presented here, the population size is 2000 (Np=2000) and the algorithm is run for 4000 generations (Ng=4000). Since the offspring has to be different from its parent, at least one of the features in the set must be replaced. The probability that a second feature will be replaced linearly decreases from 0.5 to 0.01 with each generation.

Because this modified algorithm requires that all members of the initial parent population and all generated offspring be unique, the final population will contain Np unique sets of J features that have survived because of a low overall cost. The best members of this population can be examined to determine if a small number of features are regularly used. If so, these features may represent possible biomarkers. The single set of J features with the lowest overall cost for a given value of K is used to predict the class of each of the samples in the testing set. Each sample in the testing set will be assigned a probability of being cancerous, healthy, or undetermined, and the classification with the highest probability is used (Maximum Likelihood with a minimum of 3% difference between the highest and second highest probability). The search for possible biomarkers examines the features used in the best classifier as well as important features selected from the top 100 classifiers in the final population. A feature is designated as important if it is used in 13 or more of the top 25 models and/or 50 or more of the top 100 models.

The classification analysis performed in was designed more for the identification of potential biomarkers than for the creation of the best possible classifier. This in turn is contrary to several previous classification studies: here an overall scaling of each spectrum was performed once instead of scaling each feature over the set of samples or scaling over the selected set of J features. When this was combined with the selection of important peaks, where only the largest intensity peak in each read-window was used, the potential influence of random background regions in the spectrum was removed. In addition, the classifiers were only allowed to use a small number of features (2 to 5) and a relatively large number of neighbors (6 to 9), making it very difficult to produce a fortuitous separation of samples into regions containing members of the same class.

The stringency of the analytical tools was further attested by the following facts: for 12 patient samples in the validation set, the spectra were deemed too different for averaging. Hence, each patient was characterized by two individual spectra. Therefore, subjects were assigned to either one of the groups only if 32 iterations resulted in identical results. This was successful for nine subjects. In three cases, the results were not consistent and therefore the subjects were not further considered for classification. In 70.7% of all 976 iterations tested (i.e., 16 models tested for all independent spectra, n=70), the value of the maximum likelihood exceeded 90%.

Example 2

A discovery set of sera from patients with colorectal malignancy (n=58) and healthy control individuals (n=32) were screened for potential differences using surface-enhanced laser desorption/ionization time-of-flight mass spectrometry (SELDI-TOF MS). Candidate proteins were identified, and their expression levels validated in independent sample sets using a specific immunoassay (ELISA).

Utilizing class comparison and custom developed algorithms several m/z values were identified that were differentially expressed between the malignant samples and the healthy controls of the discovery set. Characterization of the most prominent m/z values revealed a member of the complement system, the stable form of C3a anaphylatoxin, e.g., C3a-desArg. Based on a specific ELISA, serum levels of complement C3a-desArg predicted the presence of colorectal malignancy in a blinded validation set (n=59) with a sensitivity of 96.8% and a specificity of 96.2%. Increased serum levels were also detected in 86.1% of independently collected sera from patients with colorectal adenomas (n=36), while only 5.6% were classified as normal.

Complement C3a-desArg is present at significantly higher levels in serum from patients with colorectal adenomas (p<0.0001) and carcinomas (p<0.0001) than in healthy individuals. This suggests that quantification of C3a-desArg levels could ameliorate existing screening tests for colorectal cancer.

Study Population.

149 serum samples were collected at the Department of Surgery, University Hospital Schleswig-Holstein, Campus Lübeck, Germany, consisting of a discovery set of 32 healthy controls and 58 patients with colorectal malignancy and an independently collected, non-overlapping, blinded validation set of 59 samples. Peripheral blood samples were collected in adherence with protocols approved by the local Institutional Ethical Review Board as follows: blood from cancer patients was collected from patients during the initial presentation at the hospital, which in our clinic precedes the day of surgery by about four to five days. These patients were not fasting nor were they at the time of phlebotomy admitted to the hospital and therefore not exposed to specific environmental factors. The healthy control group was comprised of medical personnel, that was also not-fasting at time of blood collection. Blood was drawn into serum tubes (S-Monovette®, Sarstedt, Nümbrecht, Germany), immediately stored on ice until serum preparation was performed within two hours after collection. Samples were then stored at −20° C. Clinical data are summarized in Table 5A. In addition to the collection of serum samples for SELDI-TOF MS-based protein profiling, we collected a set of samples from patients with colorectal polyps (n=36). These samples were collected at the Department of Internal Medicine at the University Hospital Schleswig-Holstein, Campus Lübeck, prior to an explorative colonoscopy. These samples were used for quantification of serum levels of complement C3a using an ELISA test only (see below). The clinical data are provided in Table 5B.

TABLE 5A

Clinical parameter of samples in the discovery set and the blinded validation set.

| | | Discovery Set (n = 90) | | Validation Set (n = 59) | |
|---|---|---|---|---|---|
| | | Malignancy | Control | Malignancy | Control |
| Patients | | n = 58 | n = 32 | n = 38 | n = 21 |
| Tumor (T), | | (T = 38, | | (T = 17, | |
| Metastasis (M) | | M = 20) | | M = 21) | |
| SELDI-TOF MS | | n = 69 | n = 39 | n = 76 | n = 42 |
| Tumor (T), | | (T = 46, | | (T = 34, | |
| Metastasis (M) | | M = 23) | | M = 42) | |
| Sex | Female | 26 | 16 | 11 | 12 |
| | Male | 32 | 16 | 27 | 9 |
| Age | (average in years) | 63.05 | 31.34 | 65.07 | 37.33 |
| | (range in years) | (39-81) | (19-43) | (42-81) | (26-61) |
| UICC | UICC I | 8 | | 5 | |
| Staging | UICC II | 11 | | 4 | |
| | UICC III | 18 | | 3 | |
| | UICC IV | 21 | | 26 | |
| TNM | T1 | 2 | | 2 | |
| Staging | T2 | 8 | | 4 | |
| | T3 | 23 | | 10 | |
| | T4 | 5 | | 1 | |
| Localization | Cecum | 1 | | 1 | |
| | Ascending | 0 | | 2 | |
| | Transverse | 1 | | 0 | |
| | Descending | 0 | | 1 | |
| | Sigmoid | 12 | | 5 | |
| | Rectum | 24 | | 8 | |
| Metastasis/ | Liver | 8 | | 17 | |
| Recurrency | Lung | 5 | | 1 | |
| | Liver&Lung | 3 | | 2 | |
| | Recurrency | 4 | | 1 | |

TABLE 5B

Clinical parameters for 36 serum samples from patients with colorectal polyps.

| Case | Age | Sex | Polyp size | Polyp location | Histology | Dyplasia | Synchr. polyps | ELISA Adj. Conc. ng/ml | CV % | Std. Dev. |
|---|---|---|---|---|---|---|---|---|---|---|
| 1 | 63 | m | 20 mm | 3 | Hyperplastic | No | 0 | 28317.853 | 12.2 | 0.345 |
| 2 | 75 | f | 16 mm | 3 | Tubular | Lowgrade | 0 | 50345.413 | 3.6 | 0.179 |
| 3 | 63 | m | 12 mm | 2 | Tubular | Lowgrade | 0 | 44735.147 | 10.5 | 0.47 |
| 4 | 68 | f | 30 mm | n.a. | Tubulovillous | Lowgrade | 0 | 33889.272 | 4.4 | 0.149 |
| 5 | 86 | f | 4 mm | 3 | Tubulovillous | Lowgrade | 2 | 22058.816 | 4.4 | 0.098 |
| 6 | 75 | m | 15 mm | 3 | Tubulovillous | Lowgrade | 0 | 5648.808 | 5.3 | 0.03 |
| 7 | 80 | f | 15 mm | 3 | Tubular | Lowgrade | 3 | 15112.206 | 10.7 | 0.162 |
| 8 | 55 | f | 7 mm | 3 | Tubular | Lowgrade | 3 | 17698.282 | 15.2 | 0.268 |
| 9 | 89 | f | 2 mm | 3 | Tubular | Cis | 1 | 20257.066 | 12.8 | 0.259 |
| 10 | 70 | f | 10 mm | 3 | Tubulovillous | Lowgrade | 0 | 28649.786 | 15 | 0.429 |
| 11 | 53 | f | 8 mm | 0 | Tubulovillous | Lowgrade | 0 | 36740.409 | 7.7 | 0.281 |
| 12 | 78 | m | 9 mm | 0 | n.a. | Cis | 0 | 27534.233 | 14.5 | 0.4 |
| 13 | 74 | f | 6 mm | 3 | Tubular | Lowgrade | 0 | 19772.251 | 14.7 | 0.291 |
| 14 | 73 | m | 2 mm | 0 and 3 | Tubular | Lowgrade | 6 | 24323.259 | 1.9 | 0.046 |
| 15 | 71 | m | n.a. | 0 and 3 | Tubular | Lowgrade | 5 | 11869.255 | 6.6 | 0.078 |
| 16 | 75 | m | 5 mm | n.a. | n.a. | n.a. | 0 | 17289.496 | 11.9 | 0.207 |
| 17 | 67 | f | 3 mm | 0 | Hyperplastic | No | 0 | 25875.368 | 8.1 | 0.209 |
| 18 | 61 | f | 2 mm | 3 | Hyperplastic | No | 0 | 15661.015 | 12.9 | 0.201 |
| 19 | 76 | m | 2 mm | 0 and 3 | Tubular | Lowgrade | 3 | 15655.595 | 1.2 | 0.02 |
| 20 | 62 | m | 2 mm | 3 | Hyperplastic | No | 3 | 21696.217 | 11.9 | 0.257 |
| 21 | 69 | m | 3 mm | 3 | Hyperplastic | No | 0 | 32292.145 | 7.1 | 0.228 |
| 22 | 62 | m | 7 mm | 0 and 3 | Tubulovillous | Lowgrade | 3 | 16996.113 | 6.7 | 0.114 |
| 23 | 79 | f | 3 mm | 3 | Tubular | Lowgrade | 0 | 29859.718 | 8.3 | 0.247 |
| 24 | 66 | f | 6 mm | 0 and 3 | Tubulovillous | Lowgrade | 60 | 24894.408 | 5.9 | 0.146 |
| 25 | 81 | m | 5 mm | 0 | Tubulovillous | Lowgrade | 3 | 23211.359 | 6.4 | 0.148 |
| 26 | 47 | f | 2 mm | 3 | Hyperplastic | No | 5 | 20885.996 | 5.6 | 0.117 |
| 27 | 71 | m | 5 mm | 3 | Hyperplastic | No | 2 | 18776.944 | 6.1 | 0.115 |
| 28 | 88 | f | 2 mm | 0, 2 and 3 | Tubular | Lowgrade | 7 | 9122.904 | 2.4 | 0.022 |
| 29 | 62 | m | 15 mm | 0 | Tubulovillous | Lowgrade | 0 | 15495.583 | 4.4 | 0.069 |
| 30 | 71 | m | 10 mm | 3 | Tubular | Lowgrade | 4 | 18287.728 | 10 | 0.183 |
| 31 | 52 | f | 3 mm | 0 and 3 | Hyperplastic | No | 3 | 11967.37 | 13.5 | 0.162 |
| 32 | 64 | m | 22 mm | 1 and 3 | Tubulovillous | Lowgrade | 4 | 17067.89 | 5.2 | 0.089 |
| 33 | 54 | m | 15 mm | 1 and 3 | Tubular | Lowgrade | 2 | 13206.723 | 5.6 | 0.074 |
| 34 | 69 | m | 10 mm | 1 and 3 | Tubular | Lowgrade | 3 | 42076.839 | 10.9 | 0.459 |
| 35 | 67 | m | 15 mm | 0 and 3 | Tubulovillous | Lowgrade | 4 | 18987.849 | 4 | 0.075 |
| 36 | 53 | f | 7 mm | 3 | Tubulovillous | Lowgrade | 0 | 29158.652 | 4.2 | 0.122 |

0 = cecum, ascending colon, right flexure;
1 = transverse colon and left flexure;
2 = descending colon;
3 = sigmoid colon and rectum,
n.a. = not analyzed.

Sample Preparation.

Non-fractionated, total serum samples were processed using two types of ProteinChip® Arrays, immobilized metal affinity capture (IMAC3) and weak cationic exchange (WCX2) arrays, according to protocols provided by the manufacturer (Ciphergen Biosystems, Inc., Fremont, Calif.). All samples were randomized; duplicates were analyzed on separate ProteinChip® Arrays. Both types of ProteinChip Arrays were analyzed on the ProteinChip Biology System II (PBSII) SELDI-TOF mass spectrometer (Ciphergen). Mass accuracy was assessed daily through external calibration with All-in-1 Peptide and All-in-1 Protein standards (Ciphergen). The arrays were analyzed using the following PBSII automated settings: laser intensities 215 (IMAC3) and 220 (WCX2), detector sensitivity 8, focus mass 5000, m/z range 0-200,000, 130 averaged laser shots per sample spectrum. Data were collected using Ciphergen ProteinChip® software version 3.0.2.

Method of Examination.

The ProteinChip® Array data were treated by an initial truncation of the spectra to eliminate m/z values below 1500 Da. After scaling each spectrum to a constant total ion current, the spectra were combined to identify peak regions with sufficient intensity. This conservative approach dramatically reduced the SELDI-TOF MS data points to 305 significant regions on the IMAC3 array, and 322 significant regions on the WCX2 array, therefore reducing probability of chance fitting of data[16,17]. The spectra of the two array surfaces were then combined, such that each spectrum presented 627 features. It was then determined whether the two technical repeats per serum sample should be averaged or kept as duplicates. Outlier detection identified eight spectra that were excluded from subsequent analysis. Only discovery set spectra (69 cancerous and 39 controls) were used to identify features that distinguish malignant sera from control sera. Then a total of 11 independent methods were applied with the rationale that a true biomarker will appear not only in one but several analytical algorithms as a strong discriminative feature.

Five of these different methods were used to determine how malignant sera could be separated from healthy control samples based only on individual features. In addition, evolutionary programming in six sets of 16 runs was used to test how well features could separate in a pair-wise concerted form, employing average-linkage (ALC) and complete-linkage (CLC) clustering algorithms as well as Distance-Dependent K-Nearest Neighbors (DD-KNN)[18]. Here, the Euclidian distance metric was used with either absolute differences (AD) or relative differences (RD) in the intensities of the chosen set of features. Further information on all of these methods is available in supplementary Methods. Based on all methods, a total of 21 features were selected upon scoring in the top five models by any of the methods that examined individual features, or when appearing in the best model or regular appearance in the top 100 models at least five times in a set of 16 runs 5. This set of 21 features was then used to identify representative peaks in the spectrum by finding all features whose intensities have a sufficient correlation to those listed in supplementary Table 5 (r>0.70) and then visually inspecting the raw spectra. This produced a set of 33 peaks (18 from the IMAC3 array and 15 from the WCX2 array) that clustered into 9 groups. The intensities of the peaks in each group are shown in supplementary FIG. 1. The results on the IMAC array show that the peaks at 9148.7 and 8941.1 were identified by 10 and eight of the 11 methods, respectively, and appeared to have a high discriminating value. The peak at 8941.1 has a higher intensity than the 9148.7 peak (maximum intensities are 246.3 and 78.8, respectively), suggesting that the former represents the major serum state of this protein product while the latter represents some modified form (which was confirmed after protein identification). All analytical procedures were completed before our clinical collaborators in Lübeck, Germany, decoded patient diagnoses of the validation set.

Protein Identification.

Serum samples were fractionated on an anion exchange resin (Q HyperD® F, Pall Corporation, East Hill, N.Y.). The resulting fractions were further enriched using YM-30 Microcon filtration units (Millipore Inc., Bedford, Mass.) or additionally purified by reverse phase chromatography using RPC Poly-Bio beads (Polymer Laboratories Inc., Amherst, Mass.). The chromatographic fractions were monitored by SELDI-TOF MS. Enriched fractions were finally purified by SDS-PAGE (Invitrogen, Carlsbad, Calif.). Colloidal Blue stained bands were excised from gels. Whole bands of interest were extracted from gels with 50% formic acid, 25% acetonitrile, 15% isopropanol, and 10% water 19 and reanalyzed using the SELDI-TOF MS to confirm that masses of proteins from SDS-PAGE bands correspond to masses of selected biomarkers/features. Extracts were evaporated in vacuum and in-solution digested with trypsin[19]. Tryptic digests were analyzed using tandem mass spectrometer Q-TOF2 (Waters-Micromass Inc., Milford, Mass.) equipped with PCI-1000 ProteinChip Interface (Ciphergen). Spectra were collected from 1 to 3 kDa in single MS mode. After reviewing the spectra, specific ions were analyzed by MS/MS. The collision-induced dissociation spectra were submitted to the database-mining tool Mascot (Matrix Science Inc., Boston, Mass.) for identification.

Identity of biomarkers was confirmed by ProteinChip immunoassay or beads-based immunoassay. In the first case, a specific antibody was cross-linked to the PS20 ProteinChip array. The crude serum was incubated on spots with immobilized antibody, unbound proteins were removed by multiple washes, and the specifically captured proteins were analyzed directly using the ProteinChip Reader[20,21]. In the second approach, 2 µl of Protein A Hyper D beads (Pall Corporation) were loaded with a specific antibody. Beads were washed three times with Phosphate Buffered Saline (PBS) to remove unbound proteins. 2-5 µl serum samples diluted to 50 µl in PBS were bound to the beads for 30 min at room temperature. The beads were washed three times with PBS and once with water. Bound proteins were eluted from the beads with 0.1 M acetic acid. Eluted fractions were analyzed by SELDI-TOF MS using NP20 ProteinChip Arrays.

ELISA Methods.

All measurements of serum concentration for complement C3a and complement C3a-desArg were performed using the OptEIA Human C3a ELISA kit (BD Biosciences Pharmigen, San Diego, Calif.). In accordance with the manufacturer's recommendations, all serum samples were examined at a dilution of 1:1000 to ensure signal in the linear range of the reference standard curve. Using this ELISA kit, physiological serum levels of complement C3a-desArg are in the range of 8,707.2±1,797.3 ng/ml. Analyses for each serum sample and reference standard in all ELISA tests were performed in triplicate. The mean coefficient of variation (CV) value for serum analyses of the complement C3a ELISA test was 5.61%±3.66. All ELISA tests were performed using the Ultrawash Plus Plate Washer (Dynex, Chantilly, Va.) and the VersaMax Microplate Reader (Molecular Devices, Sunnyvale, Calif.).

Figure 5:
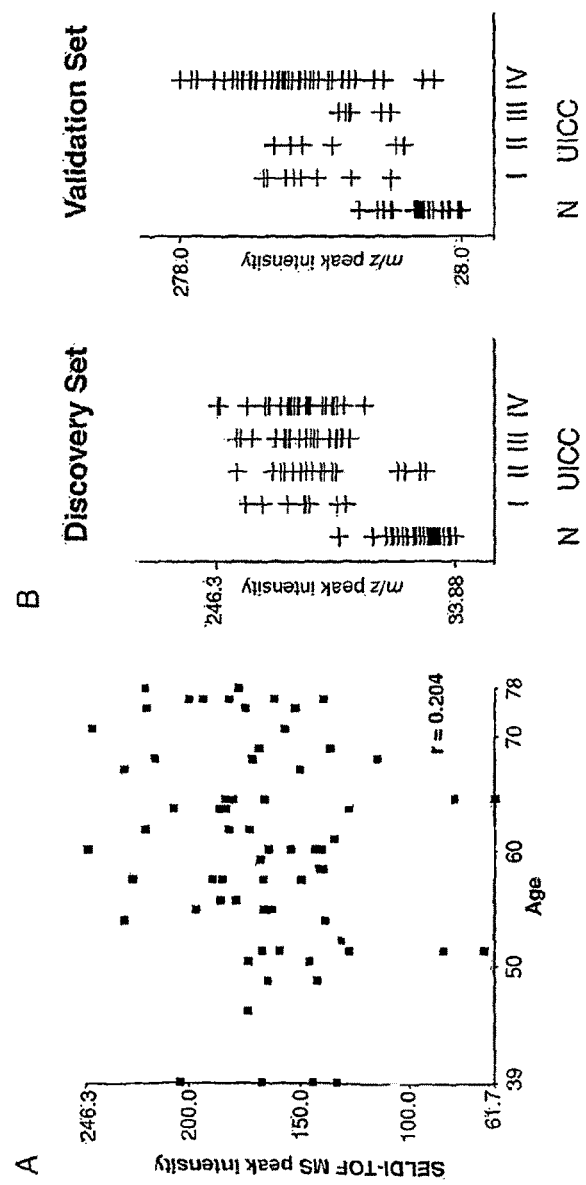
FIG. 5A depicts a scatter plot of SELDI-TOF MS-based m/z intensities at 8941.1 and age of patients. A Pearson's correlation coefficient of expression levels and age of r=0.204 indicated that there is no correlation. B depicts a summary of the SELDI-TOF MS-based values for the peak intensity at 8941.1 of the discovery and the validation set. Note that the peak intensities do not correlate with the UICC stage in either of the samples. SELDI-TOF MS values for 8941.1 are lower in healthy individuals (N).

Presented herein is a comprehensive evaluation of serum protein patterns in an effort to identify biomarkers for colon tumors. FIG. 1A presents a summary of the experimental setup. In the first step of the experimental procedures sera from 32 healthy controls and 58 sera of patients were screened with colorectal malignancy using SELDI-TOF mass spectrometry. Following truncation of spectra and normalization SELDI-TOF MS revealed m/z values on the IMAC3 array at 8941.1 Da and 9148.7 Da, which appeared to be the strongest discriminative features. These findings were corroborated by the identification of a corresponding peak from the WCX2 array surface at 8937.6 Da (r=0.811, p<0.0001). FIG. 1B exemplarily shows a SELDI-TOF (IMAC3 array) spectrum from a normal sample and a cancer sample covering the m/z values at 8941.1 and 9148.7 Da. Since the control sera were collected from significantly younger individuals as compared to the malignant sera (Table 5A) were analyzed for each selected m/z value for the possibility that the observed differences might simply be a reflection of age. No age-dependent expression of any of these m/z values were detected in the cancer samples of the discovery set; for instance, the m/z value at 8941.1 revealed a Pearson's correlation coefficient of expression levels and age of r=0.204, showing that there is no correlation between expression levels and age (FIG. 5A). The analysis of the discovery set therefore suggested that serum profiling using SELDI-TOF MS identifies protein peaks that allow the discernment of patients with colorectal malignancy from control individuals in our collection of sera. To exclude fortuitous separation of the malignant samples from healthy controls in the discovery set, the predictive value of the 8941.1 Da peak was then tested with an independently collected, blinded validation set consisting of 59 samples. Thirteen of the 59 samples (22.0%) received an unknown classification, i.e., the peak values were between the upper and lower thresholds. Fourty-five of the remaining 46 samples were correctly classified (sensitivity=96.9% and specificity=100%).

Early detection of cancer is a perceived clinical goal. Sixteen of the tumor samples in the discovery set tested here were UICC stage I and II, i.e., early tumors. The independent validation set contained nine such tumors. FIG. 5B shows the plot of the intensities of the m/z value at 8941.1 Da according to the UICC stage of the malignant sera compared to the control sera. The figure demonstrates that there is no correlation between peak intensity and tumor stage.

The fact that SELDI-TOF MS based serum proteome profiling revealed distinct m/z values whose discerning power was corroborated in an independent, blinded validation set prompted us to infer that these peaks indeed reflected biomarkers of colorectal malignancy. Therefore protein identification of the most prominent features were proceeded with.

Figure 6:
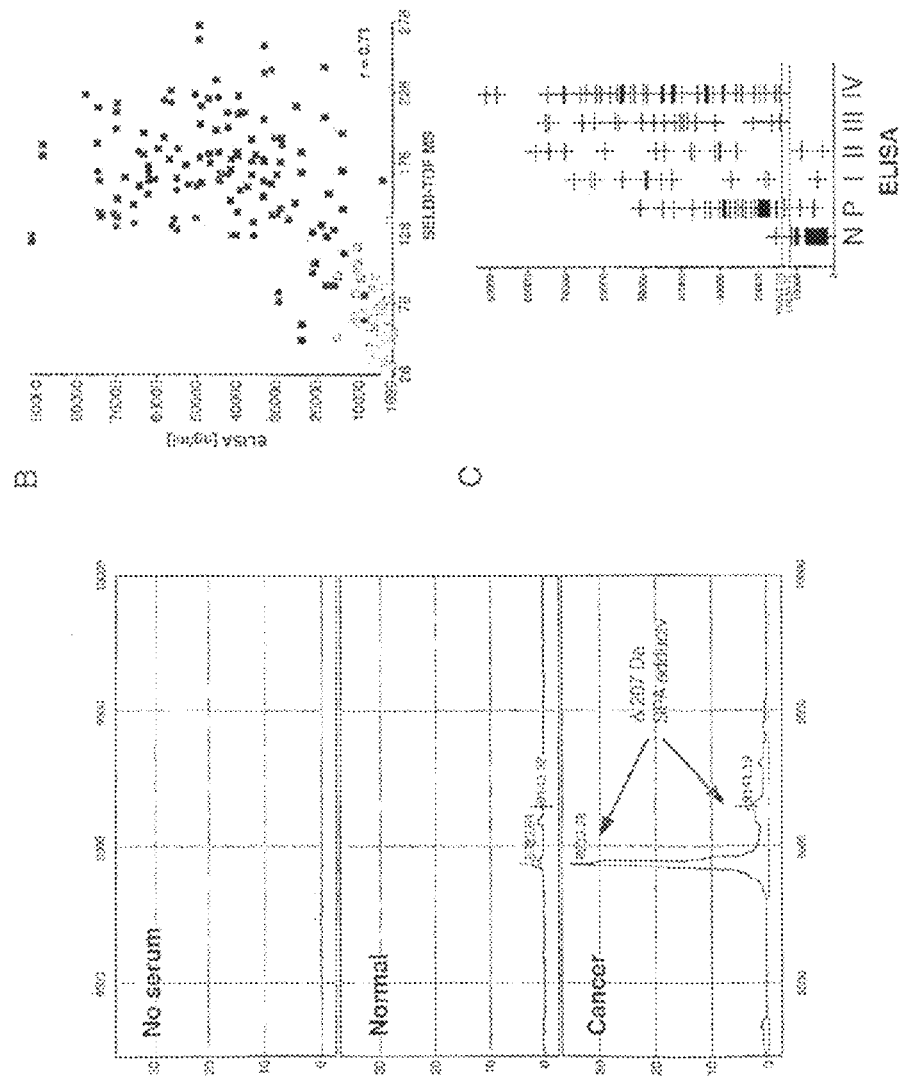
FIG. 6A depicts an immunoassay with an antibody against complement C3a-desArg reveals the identity of this protein at the prominent SELDI-TOF MS-derived m/z values of 8941.1 and 9148.7. The analysis confirms increased expression of complement C3a-desArg. (8933.28) in serum from cancer patients compared to serum from healthy individuals (Normal). The peak at 9141.19 is the expected matrix-induced adduct.
FIG. 6B depicts a scatter plot of SELDI-TOF MS-based measured intensities for the m/z intensities at 8941.1 and ELISA data for C3a-desArg. The regression analysis revealed good correlation between the SELDI-TOF MS-derived data and quantification of protein concentration with the immunoassay (r=0.71). The lighter squares indicate values from normal individuals, while the darker squares those from patients with colorectal cancer.
FIG. 6C depicts a summary of all ELISA values for complement C3a-desArg for the healthy individuals (N), sera from patients with colorectal adenomas (P), and with colorectal carcinomas according to UICC stage.

Identified were complement C3a-desArg at the peaks with m/z of 8941.1 and 9148.7 (the peak at 9148.7 is the expected satellite peak of C3a-desArg and reflects the sinapinic acid adduct caused by matrix-assisted ionization). C3a-desArg is the stable form of C3a in serum[22]. The results are presented in FIG. 6A. Next confirmed was the SELDI-TOF MS based results using an independent method for protein quantification. Serum levels of complement C3a-desArg were assessed using a commercially available ELISA test (this ELISA detects both C3a and its derivative C3a-desArg, which is the stable form of the protein in serum). After SELDI-TOF MS analysis and protein identification, sufficient serum volumes were left for 57 cancer samples and 32 normal samples of the discovery. Serum levels were also determined for all 38 malignant samples and 21 normal samples in the validation set. The results from both sets were then compared to the intensity values obtained from the SELDI-TOF spectra. The results are presented as a scatter plot in FIG. 6B. The regression analysis revealed good correlation between the SELDI-TOF MS derived data and quantification of protein concentration with the immunoassay (r=0.71). Using solely the serum levels determined with the ELISA test for C3a-desArg in the discovery set, not taking into consideration any of the additional SELDI-TOF MS peaks, nor any values from the validation set, threshold values for the prediction of malignancy were determined that were then applied to the validation set. The threshold values were determined by the intensity at which the probability of belonging to the malignant or normal group equals 60% in a 6-neighbor DD-KNN model. According to these criteria, the serum threshold for healthy individuals was equal or lower than 11,842 ng/ml and equal or higher than 17,637 ng/ml for individuals with colon malignancy. Applying these thresholds to the samples of the validation set, 35 of the malignant samples were correctly predicted to be malignant; none was predicted to be normal, while three samples could not be assigned to either group (because the values were between the lower and higher threshold of the serum levels). None of the normal samples was classified as malignant, 19 of 21 were correctly classified as normal, while two samples could not be predicted. When these thresholds were then applied to the samples in the discovery set, fewer samples could be correctly assigned to the respective groups: three of the 57 cancerous samples in the discovery set were predicted to be normal and three others could not be predicted; however, all 32 normal samples in the discovery set were predicted to be normal (Table 6A).

TABLE 6A

Prediction results of samples in the validation set

Thresholds based on discovery set ELISA values only 11,842 and 17,637 ng/ml

| | Validation set | | Discovery set | | |
| --- | --- | --- | --- | --- | --- |
| | Malignant n = 38 | Normal n = 21 | Malignant n = 57 | Normal n = 32 | Polyps n = 36 |
| Predicted as malignant | 35 | 0 | 51 | 0 | 24 |
| Predicted as normal | 0 | 19 | 3 | 32 | 2 |
| Not predictable | 3 | 2 | 3 | 0 | 10 |

The convincing performance of C3a-desArg indicating the presence of colorectal carcinomas prompted us to explore whether this marker would also be useful for the detection of colorectal adenomas. Towards this end, sera from 36 patients were collected for which the presence of a polyp was determined by colonoscopy. Sera from these patients were not analyzed using SELDI-TOF MS, but solely by means of ELISA for complement C3a-desArg. The ELISA test results for all polyp sera are included in FIG. 6C. The mean serum levels of C3a-desArg in patients with polyps (22,928.2±9,901.8 ng/ml) were lower than the levels observed in patients with invasive carcinomas (43,646.6±18,963.7 ng/ml), however, significantly increased over mean serum levels in healthy controls (5,139.3±3,233.1 ng/ml). The BD OpEIA™ Human C3a ELISA kit that was used here reports a mean C3a-desArg serum concentration in healthy individuals of 8,707.2±1,797.3 ng/ml. In analogy to the algorithm described above, the data from the discovery set of 89 samples was utilized to predict the presence of colorectal adenoma (i.e., lower thresholds of 11,842 ng/ml and higher thresholds of 17,637 ng/ml). With these thresholds 24 of the 36 patients with adenomas showed serum C3a-desArg levels above the set threshold, two revealed levels that suggested that they were normal, and 10 samples were positioned between the upper and lower thresholds. This assessment changed when the data from the validation set of 59 patients were included in calculating classification thresholds, which were then below 11,566 ng/ml for normal and above 13,652 ng/ml for cancer samples. Three of 95 cancer samples of the discovery and validation sets were now classified as normal and 92 were correctly classified, while 51 of 53 normal samples were correctly classified and the remaining two were misclassified. There were no non-classifiable samples. The sensitivity is 96.8%, and the specificity 96.2%. A positive predictive value of 97.8% was calculated, and a negative predictive value of 94.4%. In the adenoma serum collection, now 31 samples showed levels above the cutoff, two were characterized as normal, and three showed C3a-desArg serum levels between the cutoff values (see Table 6B for a summary). a correlation of serum C3a-desArg levels was not observed with the size of the polyps or with the grade of dysplasia. The ELISA values for all 184 samples analyzed here are displayed in FIG. 6C.

TABLE 6B

Prediction results of combined samples

Thresholds based on combined discovery and validation set ELISA values 11,566 and 13,652 ng/ml Validation and discovery set combined

| | Malignant n = 95 | Normal n = 53 | | Polyps n = 36 |
| --- | --- | --- | --- | --- |
| Predicted as malignant | 92 | 2 | Positive predictive value 97.8% | 31 |
| Predicted as normal | 3 | 51 | Negative predictive value 94.4% | 2 |
| Not predictable | 0 | 0 | Not predictable 0% | 3 |
| | Sensitivity 96.8% | Specificity 96.2% | | |

Presented herein are methods for SELDI-TOF MS based serum protein profiling revealing certain m/z values that allow discernment of sera from patients with and without colorectal cancer. The subsequent protein identification revealed complement C3a-desArg as the determining protein that allows prediction of the presence of malignant colorectal disease with a sensitivity of 96.8% and a specificity of 96.2%. The marker also proved useful when applied to an additional independent sample set consisting of sera from patients with colorectal adenomas, in which 86.1% of the adenoma samples revealed serum levels of complement C3a-desArg above the previously determined threshold for cancer samples, 8.3% were undetermined, and only 5.6% were classified as normal.

Disease associated mortality rates of colorectal carcinomas remain disturbingly high[1]. This is mainly attributable to late detection. The gap between the general possibility of early detection and the persistent high mortality rates is due to limited sensitivity or specificity of existing tests, such as screening for fecal occult blood (FOBT)[2], or due to an unfortunate lack of compliance for others, for instance colonoscopy[3,4]. Therefore, several additional approaches for early detection are being pursued, such as the detection of genetically or epigenetically altered genes in stool samples[23,24], and the presence of cancer cells or abnormal proteins in the peripheral blood[25]. While promising, none of these approaches has resulted in the implementation of complementary screening tests to digital rectal examination, colonoscopy, and FOBT.

Proteomic technologies have developed rapidly over the past few years and approaches for the parallel interrogation of multiple proteins in tissue or body fluids have become possible[7,8,25]. Comparable to the developments in genomics, such technologies now allow screening for differential patterns in normal and diseased states without a priori knowledge of specific alterations. One such screening platform is based on a protein array or biochip technology, where multiple proteins are attached to solid surfaces[14]. For instance, SELDI-TOF MS based screening enables the separation and at least partial characterization of multiple proteins in tissue and serum samples. The results can then be used to derive at patterns of spectra of multiple proteins that are specific for a certain disease state. Such an approach has been applied to the identification of SELDI-TOF MS patterns that are indicative of the presence of ovarian or prostate carcinoma[10,11,13,26]. Here we have used SELDI-TOF MS to verify or falsify our hypotheses that, firstly, sera from patients with colorectal malignancy are different from normal healthy controls, and that, secondly, these differentially expressed m/z values point to relevant biomarkers. Indeed, several peaks were prominent enough to allow almost perfect separation of the two groups. However, tumor prediction in our sample set did not rely on classifiers based on SELDI-TOF spectra. Instead, and in contrast to many previous applications of SELDI-TOF MS-based serum proteome profiling, we were exclusively interested in using these SELDI-TOF spectra for the detection, characterization, and independent validation of proteins that constitute the discerning m/z values. These steps were followed by the validation of serum levels of the detected proteins using a specific immunoassay (ELISA) in an independent validation set, and in sera from patients with colorectal polyps. The initial analysis of the discovery set allowed identification of 21 discriminative features that could distinguish colorectal malignancy-associated sera from healthy control sera. Prior to protein identification, the assumption that these features are indeed bona fide biomarkers was tested using an independently collected and blinded validation set: indeed, the separation into healthy individuals and patients with cancer was possible for more than 95% of the unknown samples. Identification of proteins at the most prominent m/z values revealed complement C3a-desArg, the stable derivative of complement C3a in serum and plasma[22], Complement C3a-desArg, also referred to as ASP (acylation-stimulating protein)[27], is an acute phase reactant and mainly produced in the liver and in adipocytes. It is involved in triglyceride storage, and associated with obesity, cardiovascular disease, diabetes, and dyslipidemia[22]. The complement system can be activated through the presence of tumor antigens[28]. One could therefore speculate that perhaps the presence of even relatively small adenomas can trigger a systematic reaction. The mechanistic link, however, between complement C3a activation and colorectal tumors remains to be established. Possibly, the observed complement activation could be at least partially involved in the paraneoplastic phenomenon of an increased thrombosis risk. We are not aware of data that support the interpretation that protein levels of complement C3a are upregulated in primary tumor samples similar to serum levels[29]. This would be consistent with the interpretation that we measure changes that are a reflection of a systematic reaction of the organism to the presence of neoplastic growth. This hypothesis could be potentially validated in animal models of colon cancer. In recently published papers, Li and colleagues had reported, among other proteins, overexpression of C3a-desArg in serum from patients with breast cancer, even though the discriminative power was lower than in our collection of seraph[30,31]. However, we cannot exclude the possibility that complement activation, as measured as increased serum levels of C3a-desArg reflect a more generalized reaction to the presence of malignant disease, rather than specifically to colon cancer. Limited previous reports on serum levels of members of the complement system are not conclusive in this regard[32].

Here we have explored the value of SELDI-TOF MS based serum proteome profiling for the detection of m/z values specific for malignant colorectal disease. The differentially expressed features were then successfully validated, which in turn prompted protein identification.

Figure 7:
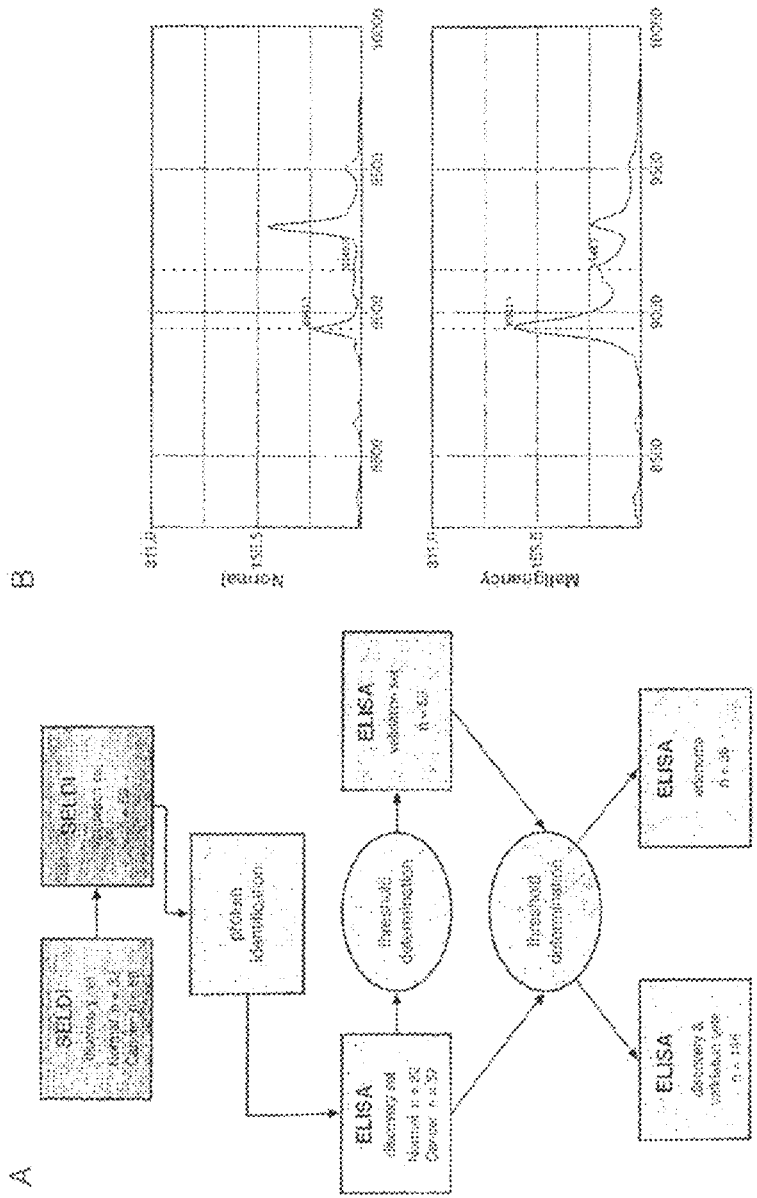
FIG. 7A depicts a flow-chart of analytical procedures for class prediction by SELDI-TOF based serum protein profiling. The first step focused on SELDI-TOF MS-based profiling of a discovery set ("SELDI discovery set" rectangle, upper left). The reproducibility of the data set was explored with an independent validation set ("SELDI validation set" rectangle, upper right). These steps were followed by protein characterization of features in prominent in/z values ("protein identification" rectangle). An ELISA test for complement C3a-desArg was used to validate all SELDI-TOF MS-based results ("ELISA validation set" rectangle, middle right) and to predict samples from a validation set and a set of sera from patients with colorectal adenomas ("ELISA discovery & validation sets" and "ELISA adenoma" rectangles, at bottom) based on serum level thresholds derived from the discovery set, or a combination of the discovery and training set ("threshold determination" ovals).
FIG. 7B depicts examples of SELDI-TOF spectra (IMAC3 ProteinChip Array) from a healthy individual (normal) and a patient with colorectal carcinoma (malignancy). The dotted lines indicate peaks at prominent m/z values at 8941.1 and 9148.7. These peaks show higher expression in the cancer sample.)

In reference to FIG. 7, a flow-chart depicts the analytical procedures for class prediction by SELDI-TOF based serum protein profiling. For example, the first step focused on SELDI-TOF MS-based profiling of a discovery set (red). The reproducibility of the data set was explored with an independent validation set (red). These steps were followed by protein characterization of features in prominent m/z values (green). An ELISA test for complement C3a-desArg was used to validate all SELDI-TOF MS-based results (blue) and to predict samples from a validation set and a set of sera from patients with colorectal adenomas (blue) based on serum level thresholds derived from the discovery set, or a combination of the discovery and training set (gray). B depicts examples of SELDI-TOF spectra (IMAC3 ProteinChip Array) from a healthy individual (normal) and a patient with colorectal carcinoma (malignancy). The dotted lines indicate peaks at prominent m/z values at 8941.1 and 9148.7. These peaks show higher expression in the cancer sample.

REFERENCES

1. O'Connell J B, Maggard M A, Ko C Y. Colon cancer survival rates with the new American Joint Committee on Cancer sixth edition staging. J Natl Cancer Inst 2004; 96:1420-5.
2. Mak T, Lalloo F, Evans D G, Hill J. Molecular stool screening for colorectal cancer. Br J Surg 2004; 91:790-800.
3. Fleischer D E, Goldberg S B, Browning T H, Cooper J N, Friedman E, Goldner F H, Keeffe E B, Smith L E. Detection and surveillance of colorectal cancer. Jama 1989; 261: 580-5.
4. Schulmann K, Reiser M, Schmiegel W. Colonic cancer and polyps. Best Pract Res Clin Gastroenterol 2002; 16:91-114.
5. Srinivas P R, Srivastava S, Hanash S, Wright G L, Jr. Proteomics in early detection of cancer. Clin Chem 2001; 47:1901-11.

6. Petricoin E F, Zoon K C, Kohn E C, Barrett J C, Liotta L A. Clinical proteomics: translating benchside promise into bedside reality. Nat Rev Drug Discov 2002; 1:683-95.
7. Conrads T P, Hood B L, Issaq H J, Veenstra T D. Proteomic patterns as a diagnostic tool for early-stage cancer: a review of its progress to a clinically relevant tool. Mol Diagn 2004; 8:77-85.
8. Hanash S. Integrated global profiling of cancer. Nat Rev Cancer 2004; 4:638-44.
9. Albertsen P C. Prostate-specific antigen: how to advise patients as the screening debate continues. Cleve Clin J Med 2005; 72:521-7.
10. Petricoin E F, Ardekani A M, Hitt B A, Levine P J, Fusaro V A, Steinberg S M, Mills G B, Simone C, Fishman D A, Kohn E C, Liotta L A. Use of proteomic patterns in serum to identify ovarian cancer. Lancet 2002; 359:572-7.
11. Petricoin E F, 3rd, Ornstein D K, Paweletz C P, Ardekani A, Hackett P S, Hitt B A, Velassco A, Trucco C, Wiegand L, Wood K, Simone C B, Levine P J, Linehan W M, Emmert-Buck M R, Steinberg S M, Kohn E C, Liotta L A. Serum proteomic patterns for detection of prostate cancer. J Natl Cancer Inst 2002; 94:1576-8.
12. Adam B L, Qu Y, Davis J W, Ward M D, Clements M A, Cazares L H, Semmes O J, Schellhammer P F, Yasui Y, Feng Z, Wright G L, Jr. Serum protein fingerprinting coupled with a pattern-matching algorithm distinguishes prostate cancer from benign prostate hyperplasia and healthy men. Cancer Res 2002; 62:3609-14.
13. Zhang Z, Bast R C, Jr., Yu Y, Li J, Sokoll L J, Rai A J, Rosenzweig J M, Cameron B, Wang Y Y, Meng X Y, Berchuck A, Van Haaften-Day C, Hacker N F, de Bruijn H W, van der Zee A G, Jacobs I J, Fung E T, Chan D W. Three biomarkers identified from serum proteomic analysis for the detection of early stage ovarian cancer. Cancer Res 2004; 64:5882-90.
14. Zhu H, Snyder M. Protein chip technology. Curr Opin Chem Biol 2003; 7:55-63.
15. Yip T T, Lomas L. SELDI ProteinChip array in oncoproteomic research. Technol Cancer Res Treat 2002; 1:273-80.
16. Ransohoff D F. Lessons from controversy: ovarian cancer screening and serum proteomics. J Natl Cancer Inst 2005; 97:315-9.
17. Baggerly K A, Morris J S, Edmonson S R, Coombes K R. Signal in noise: evaluating reported reproducibility of serum proteomic tests for ovarian cancer. J Natl Cancer Inst 2005; 97:307-9.
18. Luke B T. Nature-Inspired Methods in Chemometrics: Genetics algorithms and artificial neural networks. Elsevier, 2003.
19. Grus F H, Podust V N, Bruns K, Lackner K, Fu S, Dalmasso E A, Wirthlin A, Pfeiffer N. SELDI-TOF-MS ProteinChip array profiling of tears from patients with dry eye. Invest Opthalmol Vis Sci 2005; 46:863-76.
20. Davies H, Lomas L, Austen B. Profiling of amyloid beta peptide variants using SELDI Protein Chip arrays. Biotechniques 1999; 27:1258-61.
21. Boot R G, Verhoek M, de Fost M, Hollak C E, Maas M, Bleijlevens B, van Breemen M J, van Meurs M, Boven L A, Laman J D, Moran M T, Cox T M, Aerts J M. Marked elevation of the chemokine CCL18/PARC in Gaucher disease: a novel surrogate marker for assessing therapeutic intervention. Blood 2004; 103:33-9.
22. Cianflone K, Xia Z, Chen L Y. Critical review of acylation-stimulating protein physiology in humans and rodents. Biochim Biophys Acta 2003; 1609:127-43.
23. Laird P W. The power and the promise of DNA methylation markers. Nat Rev Cancer 2003; 3:253-66.
24. Chen W D, Han Z J, Skoletsky J, Olson J, Sah J, Myeroff L, Platzer P, Lu S, Dawson D, Willis J, Pretlow T P, Lutterbaugh J, Kasturi L, Willson J K, Rao J S, Shuber A, Markowitz S D. Detection in fecal DNA of colon cancer-specific methylation of the nonexpressed vimentin gene. J Natl Cancer Inst 2005; 97:1124-32.
25. Fung E T, Yip T T, Lomas L, Wang Z, Yip C, Meng X Y, Lin S, Zhang F, Zhang Z, Chan D W, Weinberger S R. Classification of cancer types by measuring variants of host response proteins using SELDI serum assays. Int J Cancer 2005; 115:783-9.
26. Grizzle W E, Adam B L, Bigbee W L, Conrads T P, Carroll C, Feng Z, Izbicka E, Jendoubi M, Johnsey D, Kagan J, Leach R J, McCarthy D B, Semmes O J, Srivastava S, Srivastava S, Thompson I M, Thornquist M D, Verma M, Zhang Z, Zou Z. Serum protein expression profiling for cancer detection: validation of a SELDI-based approach for prostate cancer. Dis Markers 2003; 19:185-95.
27. Baldo A, Sniderman A D, St-Luce S, Avramoglu R K, Maslowska M, Hoang B, Monge J C, Bell A, Mulay S, Cianflone K. The adipsin-acylation stimulating protein system and regulation of intracellular triglyceride synthesis. J Clin Invest 1993; 92:1543-7.
28. Verhaegen H, De Cock W, De Cree J, Verbruggen F. Increase of serum complement levels in cancer patients with progressing tumors. Cancer 1976; 38:1608-13.
29. Roblick U J, Hirschberg D, Habermann J K, Palmberg C, Becker S, Kruger S, Gustafsson M, Bruch H P, Franzen B, Ried T, Bergmann T, Auer G, Jornvall H. Sequential proteome alterations during genesis and progression of colon cancer. Cell Mol Life Sci 2004; 61:1246-55.
30. Li J, Zhang Z, Rosenzweig J, Wang Y Y, Chan D W. Proteomics and bioinformatics approaches for identification of serum biomarkers to detect breast cancer. Clin Chem 2002; 48:1296-304.
31. Li J, Orlandi R, White C N, Rosenzweig J, Zhao J, Seregni E, Morelli D, Yu Y, Meng X Y, Zhang Z, Davidson N E, Fung E T, Chan D W. Independent validation of candidate breast cancer serum biomarkers identified by mass spectrometry. Clin Chem 2005; 51:2229-35.
32. Maness P F, Orengo A. Serum complement levels in patients with digestive tract carcinomas and other neoplastic diseases. Oncology 1977; 34:87-9.
33. Diamandis E P. Analysis of serum proteomic patterns for early cancer diagnosis: drawing attention to potential problems. J Natl Cancer Inst 2004; 96:353-6.
34. Chen Y D, Zheng S, Yu J K, Hu X. Artificial neural networks analysis of surface-enhanced laser desorption/ionization mass spectra of serum protein pattern distinguishes colorectal cancer from healthy population. Clin Cancer Res 2004; 10:8380-5.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

A number of embodiments of the invention have been described. Nevertheless, it will be understood that various modifications may be made without departing from the spirit and scope of the invention. Accordingly; other embodiments are within the scope of the following claims.

What is claimed is:

1. A method of qualifying colorectal adenoma status in a subject comprising:
   (a) measuring Marker X: 9148.7 in a serum sample from the subject, wherein said measuring comprises contacting said serum sample to a biochip capable of detecting Marker X: 9148.7, and
   (b) identifying the subject as having colorectal adenoma when the Marker X: 9148.7 level is greater than 13,652 ng/mL.

2. A method for differentiating between a diagnosis of colorectal cancer and non-colorectal cancer comprising:
   (a) detecting Marker X: 9148.7 in a serum sample from a subject, and
   (b) after performing said detecting, identifying a subject as having colorectal cancer when the Marker X: 9148.7 level is greater than 13,652 ng/mL; and
   (c) administering radiation therapy to said subject identified as having colorectal cancer.

3. A method of qualifying colorectal cancer status in a subject comprising:
   (a) measuring the level of Marker X: 9148.7 in a serum sample from the subject, wherein said measuring comprises contacting said serum sample to a biochip capable of detecting Marker X: 9148.7, and
   (b) after performing said measuring, if said measured level is greater than 13,652 ng/mL, identifying the subject as having colorectal cancer.

4. A method for differentiating between a diagnosis of colorecectal cancer and non-colorectal cancer comprising:
   (a) detecting Marker X: 9148.7 in a serum sample from a subject, wherein said detecting comprises contacting said serum sample to a biochip capable of detecting Marker X: 9148.7, and
   (b) after performing said detecting, identifying the subject as having colorectal cancer when the Marker X: 9148.7 level is greater than 13,652 ng/mL.

5. The method of claim 3 or 4, wherein the subject is identified as having colorectal cancer when the Marker X: 9148.7 level is greater than 17,637 ng/mL.

6. The method of claim 3 or 4, wherein the colorectal cancer is adenocarcinoma, mucinous adenocarcinoma, signet-ring cell adenocarcinoma, squamous cell carcinoma, adenosquamous carcinoma, undifferentiated carcinoma, unclassified carcinoma, carcinoid tumors, or nonepithelial tumors.

7. A method of qualifying colorectal cancer status in a subject comprising:
   (a) measuring the level of Marker X: 9148.7 in a serum sample from the subject, and
   (b) after performing said measuring, if said measured level is greater than 13,652 ng/mL, identifying the subject as having colorectal cancer; and
   (c) administering radiation therapy to said subject identified as having colorectal cancer.

8. The method of claim 3, wherein the colorectal cancer is adenocarcinoma, mucinous adenocarcinoma, or signet-ring cell adenocarcinoma.

9. The method of claim 1 or 3, further comprising:
   (c) managing subject treatment based on the status.

10. The method of claim 9, wherein managing subject treatment is selected from ordering further diagnostic tests, administering at least one therapeutic agent, administering radiation therapy, immunotherapy, hyperthermia, surgery, surgery followed or preceded by chemotherapy and/or radiation therapy, biotherapy, and taking no further action.

11. The method of claim 10, wherein the therapeutic agent is selected from one or more of the group consisting of hypomethylating agents, farnesyltransferase inhibitors, cytokines, immunomodulatory agents, hormones, and antibodies.

12. The method of claim 10, wherein the therapeutic agent is selected from one or more of the group consisting of folic acid, fluorouracil, 5-FU irinotecan, oxaliplatin, leucovorin, levamisole, and low-dose leucovorin.

13. The method of claim 9, further comprising:
   (d) measuring at least one of Marker X: 9148.7 or Marker XIV: anaphylatoxin C3a after subject management.

14. The method of claim 3, wherein the colorectal cancer status is selected from one or more of the group consisting of the subject's risk of colorectal carcinoma, the presence or absence of carcinoma, the type of carcinoma disease, the stage of carcinoma and effectiveness of treatment.

* * * * *